United States Patent
Okuno et al.

(10) Patent No.: US 10,398,401 B2
(45) Date of Patent: Sep. 3, 2019

(54) RADIATION TOMOGRAPHY DEVICE

(71) Applicant: SHIMADZU CORPORATION, Nakagyo-Ku, Kyoto-Shi, Kyoto (JP)

(72) Inventors: Tomoharu Okuno, Kyoto (JP); Ken Shirota, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 94 days.

(21) Appl. No.: 15/307,950

(22) PCT Filed: May 1, 2014

(86) PCT No.: PCT/JP2014/062108
§ 371 (c)(1),
(2) Date: Oct. 31, 2016

(87) PCT Pub. No.: WO2015/166575
PCT Pub. Date: Nov. 5, 2015

(65) Prior Publication Data
US 2017/0055936 A1    Mar. 2, 2017

(51) Int. Cl.
*A61B 6/00* (2006.01)
*A61B 6/02* (2006.01)

(52) U.S. Cl.
CPC ............... *A61B 6/547* (2013.01); *A61B 6/02* (2013.01); *A61B 6/40* (2013.01); *A61B 6/4452* (2013.01);
(Continued)

(58) Field of Classification Search
None
See application file for complete search history.

(56) References Cited

U.S. PATENT DOCUMENTS 4,908,844 A * 3/1990 Hasegawa ............ A61B 6/0457
378/209
2002/0154728 A1 10/2002 Morita et al.
(Continued)

FOREIGN PATENT DOCUMENTS

CN    1460451    12/2003
CN    102512190    6/2012
(Continued)

OTHER PUBLICATIONS

PCT/JP2014/062108, International Search Report and Written Opinion dated Jun. 10, 2014, 7 pages—Japanese, 2 pages—English.
(Continued)

*Primary Examiner* — Hoon K Song
(74) *Attorney, Agent, or Firm* — Andrew F. Young, Esq.; Lackenbach Siegel, LLP

(57) ABSTRACT

In a radiation tomography imaging device, the imaging range calculation element 35 calculates a possible imaging range of the FPD 5 based on the imaging distance G, the irradiation swing angle θ and the movable range SP of the X-ray tube 3. The operator can preliminarily calculate the possible imaging range of the radiation detection means prior to the X-ray tomography imaging because the imaging distance, the irradiation swing angle, and the movable range SP are all predetermined parameters. The possible imaging range FP of the FPD 5 is the positional range of the FPD 5 in which the X-ray tube 3 can acquire the X-ray tomography image without moving the X-ray tube 3 to the outside of movable range. Therefore, the radiation tomography imaging can start the X-ray tomography by assuredly moving the FPD 5 within the possible imaging range by referring to the preliminarily calculated possible imaging range of the FPD 5. As results, an incident in which the X-ray tube 3 moves out of the movable range SP and interferes the floor surface
(Continued)

W and so forth can be avoided, so that the X-ray tomography imaging can be performed adequately.

17 Claims, 22 Drawing Sheets

(52) U.S. Cl.
CPC .............. *A61B 6/4464* (2013.01); *A61B 6/46* (2013.01); *A61B 6/5205* (2013.01)

(56) References Cited

U.S. PATENT DOCUMENTS

| | | | | |
|---|---|---|---|---|
| 2003/0219101 A1* | 11/2003 | Tsujii | .................. | A61B 6/0457 378/205 |
| 2016/0120495 A1* | 5/2016 | Miyazawa | ............. | A61B 6/025 378/21 |

FOREIGN PATENT DOCUMENTS

| | | |
|---|---|---|
| JP | 2002-263093 | 9/2002 |
| JP | 2012-100738 | 5/2012 |

OTHER PUBLICATIONS

CN Pat. Appln. No. 201480078388.5, Notification of Reasons for Refusal dated Nov. 27, 2018, 10 Pages—Chinese, 9 pages—English.

\* cited by examiner

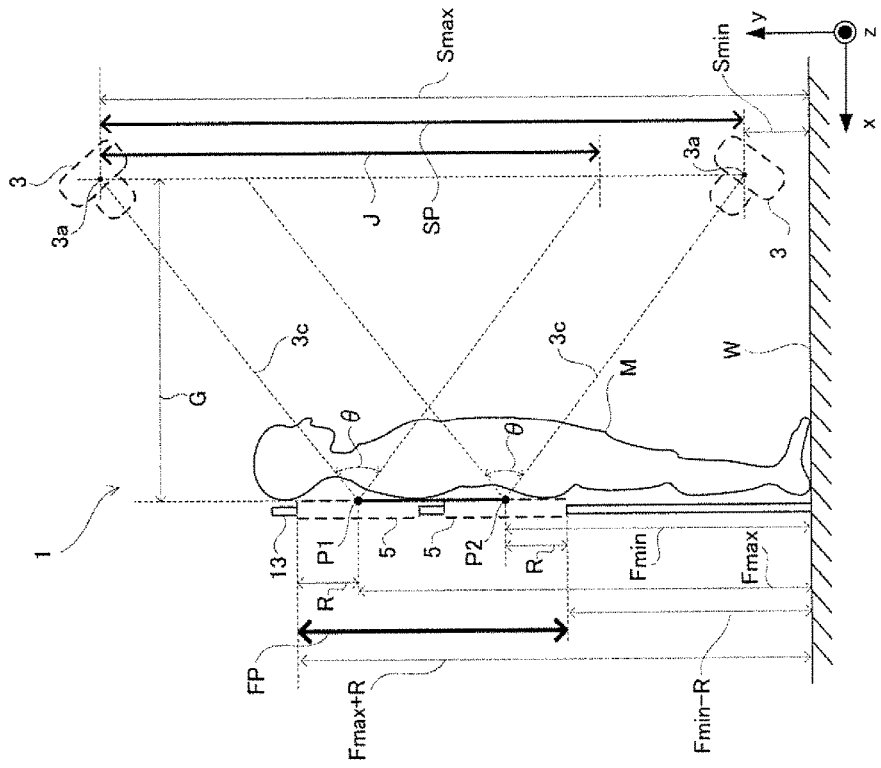
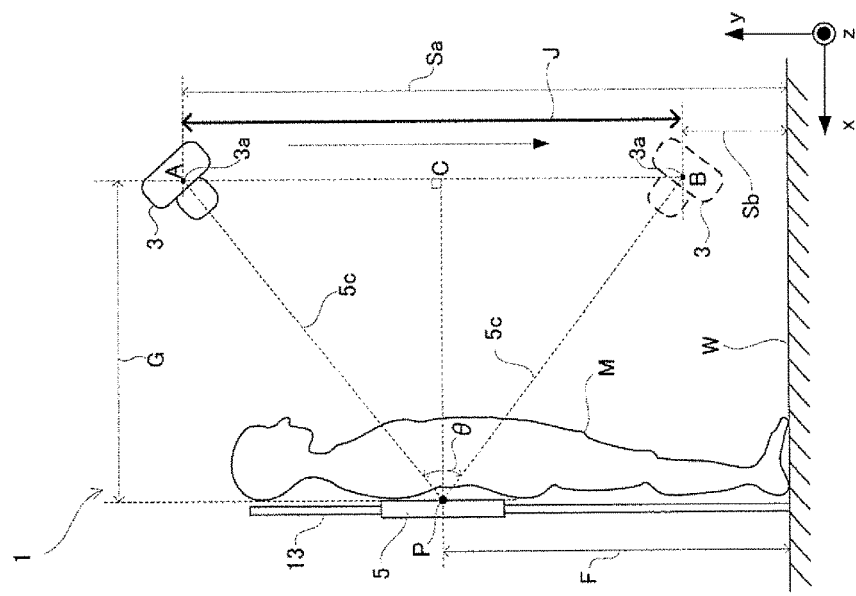
FIG. 3A
FIG. 3B

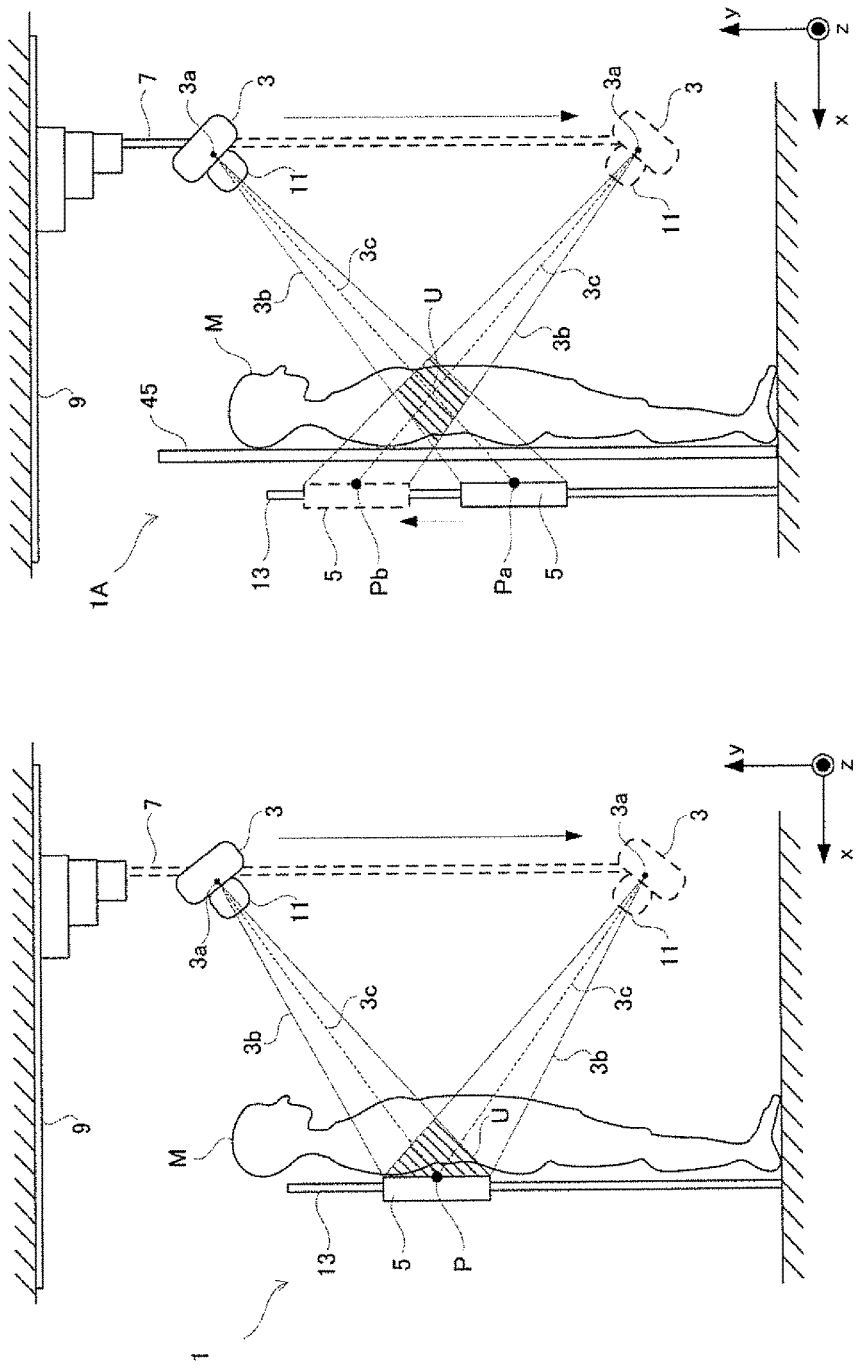

X-ray Tube Moving Velocity (Vs)

RADIATION TOMOGRAPHY DEVICE

CROSS REFERENCE TO RELATED APPLICATIONS

This application relates to and claims priority from PCT Ser. No.: PCT/JP2014/062108 filed May 1, 2014, the entire contents of which are incorporated herein by reference.

FIGURE SELECTED FOR PUBLICATION

FIG. 5

BACKGROUND OF THE INVENTION

Field of the Invention

The present invention relates to a radiation tomography device having a radiation source and a radiation detector, and particularly relates to a technology by which a positional range of the radiation detector, which enables imaging of the radiation tomography image, is automatically calculated.

Description of the Related Art

In medical fields, a radiation imaging device based on an imaging technology so-called tomosynthesis, which is a device to obtain a tomographic image of a cross section of a subject by utilizing a radiation, has been used (Patent Document 1, 2.) As for such radiation tomographic device, a radiation source and a radiation detector are in place facing each other as if sandwiching the subject. When imaging a series of radiation images, the radiation source is being moved relative to the radiation detector. Then, a radiation tomographic image of the subject is reconstructed based on the obtained series of radiation images by a digital processing and then is displayed on a display element e.g., a monitor. In addition, a flat panel display (FPD) is primarily used for the radiation detector.

Referring to FIG. 20A, 20B, the inventor set forth the structure of a conventional radiation tomographic imaging device. The conventional radiation tomography 100 includes a support post 101, a radiation source 103, a FPD 105 and a moving mechanism 107. The radiation source 103 is installed to the support post, which is based on the ceiling of the examination room, to be movable freely.

Further, as indicated by the arrow referring to FIG. 20A, the radiation source 103 intermittently irradiates from the position indicated by the solid line to the position indicated by the broken line, in a y-direction, i.e., while moving to the body axis of the subject M, the radiation is intermittently irradiated to the subject M from the focus point 103a relative to the subject M. The FPD 105 detects the radiation irradiated from the focus point 103a and passed through the subject M, and output as a radiation detection signal. And the radiation image of the subject M is generated based on the detection signal output from the FPD 105.

The moving mechanism 107 controls the movement of the radiation source 103 in the y-direction and also tilts the radiation source 103 relative to the y-direction so that the center axis 103b of the radiation beam irradiated from the focus point 103a can always pass the center point P of the detection face of the FPD 105. The radiation source 103 changes sequentially an irradiation angle of the radiation interlockingly with the moving direction of the radiation source 103 in the y-direction, so that the radiation source 103 can constantly irradiate the center point P. In addition, a height from a floor surface W to the center point of the detection face of the FPD 105 is F.

Specifically, the radiation source 103 irradiates sequentially the radiation while sequentially changing the swing angle thereof, so that a number of radiation images due to the different incident angles relative to the target region can be generated. The number of acquired radiation images is reconstructed so that the radiation tomography images of the subject M of the expected cross sections can be obtained.

Referring to FIG. 20B, according to the conventional radiation tomography device 100, the moving mechanism 107 may move synchronously the radiation source 103 and the FPD 105. Specifically, the moving mechanism 107 moves the radiation source 103 and the FPD 105 and reversely each other in the y-direction so that the central axis 103b of the X-ray beam can pass the cross section center Q that is a target region. Thus, the radiation source 103 and the FPD 105 move in the opposite direction each other sandwiching the subject M while keeping the positions facing each other. In such case, a radiation image relative to the base cross section Ma including the cross section center Q and parallel to the detection face can be generated.

An enlargement factor of the acquired radiation tomography image is affected by the distance between the focus point 103a and the detection face (imaging distance) and a cross section thickness of the radiation tomography image is affected by the swing angle (irradiation swing angle) of the radiation source while intermittently irradiating the radiation. It is desired that if the enlargement factor should be smaller, the imaging distance, referring to FIG. 20A, FIG. 20B, should be longer. Further, it is desired that if the cross section thickness should be thinner, the irradiation swing angle $\theta$ should be larger.

RELATED PRIOR ART DOCUMENTS

Patent Document 1: JP 2002-263093 A1
Patent Document 2: JP 2012-100738 A1

ASPECTS AND SUMMARY OF THE INVENTION

Objects to be Solved

Nevertheless, in the case of a conventional example having such structure, following problems are remained to be solved.

Specifically, it is likely problematic for the conventional radiation tomography imaging devices because the radiation tomography imaging may not be efficiently performed depending on parameters including the height F between the floor surface W and the center point P, the imaging distance, the irradiation swing angle $\theta$ and so forth.

Depending on the structure of the radiation tomography imaging devises, the movable range of the radiation source 103 in the vertical direction is limited at most to the range between the floor and the ceiling. In addition, the radiation source 103 is a heavy stuff, so that it is required that the support post 103 to hold the radiation source 103 and the moving mechanism 107 to move the radiation source 103 must be structured strongly. Accordingly, the movable range of the radiation source 103 may be further narrowed due to such mechanical restriction Therefore, the moving range of the radiation source 103 relative to the radiation tomography may be out of the movable range of the radiation source 103 depending on values including the height F of the center point P, the radiation swing angle $\theta$ and the imaging distance G. For example, referring to FIG. 21, when the height F of the center point P is lowered, the radiation source 103 to acquire the radiation tomography image must be moved from the position indicated by the solid line to the position indicated by the broken line. In such case, the moving range of the radiation source 103, i.e., moving region of the radiation source 103, covers the range indicated by the sign J, from the position indicated by the solid line to the position indicated by the broken line relative to the radiation source 103. However, the position indicated by the broken line is below the floor surface, so that the radiation source cannot be moved to the position indicated by the broken line. Such incident takes place when the irradiation swing angle θ is wider or the imaging distance is longer.

In addition, referring to FIG. 20B, when the radiation source 103 and the FPD 105 move synchronously each other in the opposite direction, the moving region J of the radiation source 103 may be out of the movable range depending on the distance between the base cross section Ma and the detection face of the FPD 105 (cross section height.) Specifically, either the irradiation swing angle θ or the imaging distance G is the same, if the cross section height H is higher; the moving region J of the radiation source becomes narrower (FIG. 22A.) However, if the subject M moves closer to the FPD 105 so as to shorten the cross section height, the moving region J of the radiation source 103 becomes broader, so that the moving region J of the radiation source 103 may be out of the movable range of the radiation source 103 (FIG. 22B.)

Accordingly, when the moving region of the radiation source 103 extends out of the movable range and the radiation tomography imaging is conducted, the radiation source may be interfered by the ceiling or the floor. In addition, when the operator or another realizes that the moving range of the radiation source 103 is going to extend out of the movable range of the radiation source, after the radiation source starts moving, and then suspends the radiation tomography imaging, the time spent for suspended radiation tomography imaging becomes useless and wasteful. Specifically, the operator has to redo the radiation tomography imaging with an effort, so that the time required for such radiation tomography imaging can be longer. In addition, the radiation must be re-irradiated to the subject M, so that it can be problematic that the radiation exposure exposed to the subject M increases.

Considering such circumstances, the object of the present invention is to provide a radiation tomography imaging device capable of preliminarily calculating the range of the position of the FPD in which the radiation tomography imaging can be conducted.

Means for Solving the Problem

The present invention constitutes the following structure to solve such problem.

Specifically, a radiation tomography imaging device of the present invention comprises: a detection means that detects the radiation transmitted through the subject, a radiation source moving means that moves said radiation source in the body axis direction of a subject, a radiation irradiation control means that controls the radiation source so as to repeatedly irradiate the radiation while the radiation source moving means is moving the radiation source, an image generation means that generates a radiation image using the detection signal output from the radiation detection means every radiation irradiation from the radiation source, a tomography image acquisition means that acquires a radiation tomography image by reconstructing a plurality of radiation images generated by the image generation means, and a possible imaging range calculation means that calculates the possible imaging range of the radiation detection means, which is the positional range of the radiation detection means, in which the radiation source is in the movable range of the radiation source and the detection means can acquire the radiation tomography image based on a group consisting of parameters comprising an imaging distance from the focus point of the radiation source and the radiation detection means, the irradiation swing angle that is the swing angle of the radiation source while the radiation irradiation means allows the radiation source repeatedly irradiating the radiation and the movable range of the radiation source.

According to the radiation tomography imaging device of the present invention, the possible imaging range calculation means that calculates the possible imaging range of the radiation of the radiation detection means based on a group consisting of parameters comprising an imaging distance, the irradiation swing angle and the movable range of the radiation source. The imaging distance and the irradiation swing angle are any parameters that the operator determines preliminarily and arbitrarily in accordance with a cross section thickness, an enlargement factor and so forth of the radiation tomography image. And the movable range of the radiation source is a predetermined parameter in accordance with a specification of the radiation tomography imaging device. Accordingly, the operator can preliminarily calculate the possible imaging range of the radiation detection means prior to the radiation tomography imaging based on the imaging distance, the irradiation swing angle and the movable range of the radiation source.

The possible imaging range of the radiation detection means is a positional range of the radiation detection means, wherein the radiation source is in the movable range of the radiation source and the radiation detection means can acquire the radiation tomography image. Therefore, the radiation tomography imaging can start the radiation tomography by assuredly moving the radiation detection means within the possible imaging range by referring to the possible imaging range of the preliminarily calculated possible imaging range of the radiation detection means. Accordingly, an incident in which the radiation source moves out of the movable range of the radiation source and is interfered by the floor or an incident in which the radiation imaging is suspended by predicting the inference of the radiation source after the radiation tomography imaging has started can be absolutely avoided. As results, the time needed for radiation tomography imaging can be shorten by preventing the labors and the time for re-imaging, so that a radiation tomography image with a high quality can be imaged efficiently.

The present invention can constitute the following structure to achieve such purpose.

Specifically, a radiation tomography imaging device of the present invention comprises: a detection means that detects the radiation transmitted through the subject, a radiation source moving means that moves said radiation source in the body axis direction of a subject, a radiation irradiation control means that controls the radiation source so as to repeatedly irradiate the radiation while the radiation source moving means is moving the radiation source, an image generation means that generates a radiation image using the detection signal output from the radiation detection means every radiation irradiation from the radiation source, a tomography image acquisition means that acquires a radiation tomography image by reconstructing a plurality of radiation images generated by the image generation means, a detector moving means that moves in the opposite direction of the moving direction of the radiation source moved by the radiation moving means while the radiation detection means and the radiation source facing each other and sandwiching the subject, and a possible imaging range calculation means that calculates the possible imaging range of the radiation detection means, which is the positional range of the radiation detection means, in which the radiation source is in the movable range of the radiation source and the detection means can acquire the radiation tomography image based on a group consisting of parameters comprising an imaging distance from the focus point of the radiation source to the radiation detection means, the irradiation swing angle that is the swing angle of the radiation source while the radiation irradiation means allows the radiation source repeatedly irradiating the radiation and the movable range of the radiation source, and a cross section height that is a distance from the detection surface of the radiation detection means.

According to the radiation tomography imaging device of the present invention, the possible imaging range calculation means that calculates the possible imaging range of the radiation of the radiation detection means based on a group consisting of parameters comprising an imaging distance, the irradiation swing angle, the movable range of the radiation source and the cross section height. The imaging distance, the irradiation swing angle and the cross section height are any parameters that the operator determines preliminarily and arbitrarily in accordance with a cross section thickness, an enlargement factor and so forth of the radiation tomography image. And the movable range of the radiation source is a predetermined parameter in accordance with a specification of the radiation tomography imaging device. Accordingly, the operator can preliminarily calculate the possible imaging range of the radiation detection means prior to the radiation tomography imaging based on the imaging distance, the irradiation swing angle, the movable range of the radiation source and the cross section height.

The possible imaging range of the radiation detection means is a positional range of the radiation detection means, wherein the radiation source is in the movable range of the radiation source and the radiation detection means can acquire the radiation tomography image. Therefore, the radiation tomography imaging can start the radiation tomography by assuredly moving the radiation detection means within the possible imaging range by referring to the possible imaging range of the preliminarily calculated possible imaging range of the radiation detection means. Accordingly, an incident in which the radiation source moves out of the movable range of the radiation source and interferes the floor, or an incident in which the radiation imaging is suspended by predicting the inference of the radiation source after the radiation tomography imaging has started can be absolutely avoided. As results, the time needed for a radiation tomography imaging can be shorten by preventing the extra labors and the time wasting for re-imaging, so that a radiation tomography image with a high quality can be imaged efficiently.

Further, the radiation moving means moves the detector moving means in the opposite direction of the moving direction of the radiation source moved by the radiation moving means while the radiation detection means and the radiation source are facing each other and sandwiching the subject. Accordingly, a radiation image to reconstruct the radiation tomography image can be generated in the region away from the radiation detection means. Specifically, even if a target region is located in an anterior side of the subject, the radiation image can be generated adequately. Accordingly, the radiation tomography images relative to the broader range of subject, including the anterior side, can be acquired.

In addition, according to the radiation tomography imaging device of the present invention, it is desired that the group consisting of parameters further includes an acceleration distance, which is the distance while the radiation source moves during being accelerated, from the imaging preparation position of the radiation source to the imaging start position, and an deceleration distance, which is the distance while the radiation source moves during being decelerated, from the irradiation ending position of the radiation source to the imaging ending position.

According to the radiation tomography imaging device of the present invention, the group consisting of the parameters further includes the acceleration distance and the deceleration distance. The acceleration distance is the distance while the radiation source moves during being accelerated from the imaging preparation position of the radiation source to the imaging start position. The deceleration distance is the distance from the irradiation ending position of the radiation source to the imaging ending position, while the radiation source moves during being decelerated. Either acceleration distance or deceleration distance can be predetermined prior to the X-ray tomography imaging in accordance with the moving velocity of the radiation source. Accordingly, the operator can preliminarily calculate the possible imaging range of the radiation detection means prior to the radiation tomography imaging using the predetermined parameters.

Further, the radiation source moves during being accelerated from the imaging preparation position of the radiation source to the imaging start position. And the radiation source moves during being decelerated from the irradiation ending position of the radiation source to the imaging ending position. Specifically, the radiation source moves while keeping the moving velocity and repeatedly irradiating the radiation from the irradiation start position to the irradiating ending position.

According to such structure, the radiation source can intermittently irradiate X-ray while moving with a constant velocity and can generate a series of X-ray images. At this time, the moving velocity of the radiation source is constant, so that the timing when the intermittent irradiation of the X-ray to generate the series of X-ray images can be further easily calculated. Therefore, a control to image the adequate X-ray tomography images can be more accurately and further easily conducted.

In addition, according to the radiation tomography imaging device of the present invention, it is desired that an input element that inputs the group consisting of parameters is included and the possible imaging range calculation means calculates the possible imaging range of the radiation detection means is calculated based on the group consisting of the parameters input into the input element every time when the group consisting of parameters are input into the input element.

According to the radiation tomography imaging device of the present invention, an input element that inputs the group consisting of parameters consisting of an imaging distance, an irradiation swing angle and so forth is included. The possible imaging range calculation means calculates the possible imaging range of the radiation detection means based on the group consisting of the parameters newly input into the input element every time when the group consisting of parameters is input into the input element. Therefore, even if any parameter of the group consisting of the parameters is needed to be changed, the possible imaging range can be quickly calculated by inputting the group consisting of the parameters. Accordingly, the possible imaging range of the radiation detection means can be more accurately calculated prior to the radiation imaging, so that the radiation tomography imaging can be adequately and efficiently conducted.

In addition, according to the radiation tomography imaging device of the present invention, it is desired that a detector position calculation means that calculates a position of the radiation detection means is included.

According to the radiation tomography imaging device of the present invention, the detector position calculation means that calculates the position of the radiation detection means is included. Therefore, it can be decided whether the radiation detection means is positioned in the possible imaging range by referring the position of the radiation detection means calculated by the detector calculation means or not. Accordingly, an incident, in which the radiation source moves out of the movable range of the radiation source and interferes the floor and so forth, or an incident in which the radiation imaging is suspended by predicting the interference of the radiation source after the radiation tomography imaging has started, can be absolutely avoided.

In addition, according to the radiation tomography imaging device of the present invention, it is desired that an alarm means to alarm when the position of the radiation detection means calculated by the detector position calculation means is out of the possible imaging range is included.

According to the radiation tomography imaging device of the present invention, the alarm means alarm based on the position of the radiation detection means calculated by the detector position calculation means when the position of the radiation detection means is out of the possible imaging range. In such case, the operator can confirm quickly and absolutely by being aware of the alarm informing that the position of the radiation detection means is out of the radiation detection means. Accordingly, the operator can move quickly and absolutely the radiation detection means within the possible imaging range, so that the radiation tomography images having a higher quality can be imaged more efficiently.

In addition, according to the radiation tomography imaging device of the present invention, it is desired that a detector moving control means that controls the detector moving means so as to move the radiation detection means within the possible imaging range when the position of the radiation detection means calculated by the detector position calculation means is out of the possible imaging range.

According to the radiation tomography imaging device of the present invention, the detector moving control means controls the detector moving means based on the position of the radiation detection means calculated by the detector position calculation means when the position of the radiation detection means is out of the possible imaging range. The detector moving means moves the radiation detection means within the possible imaging range following the control of the detector moving control means. Therefore, even when the operator is not aware of that the position of the radiation detection means is out of the possible imaging rage, the radiation detection means can be positioned assuredly within the possible imaging range. Accordingly, the operator can move quickly and absolutely the radiation detection means within the possible imaging range, so that the radiation tomography images having a higher quality can be imaged more efficiently.

Effect of the Invention

According to the radiation tomography imaging device of the present invention, the possible imaging range calculation means that calculates the possible imaging range of the radiation of the radiation detection means based on a group consisting of parameters comprising an imaging distance, the irradiation swing angle and the movable range of the radiation source. The imaging distance and the irradiation swing angle are any parameters that the operator determines preliminarily and arbitrarily in accordance with a cross section thickness, an enlargement factor and so forth of the radiation tomography image. And the movable range of the radiation source is a predetermined parameter in accordance with a specification of the radiation tomography imaging device. Accordingly, the operator can preliminarily calculate the possible imaging range of the radiation detection means prior to the radiation tomography imaging based on the imaging distance, the irradiation swing angle and the movable range of the radiation source.

The possible imaging range of the radiation detection means is a positional range of the radiation detection means, wherein the radiation source is in the movable range of the radiation source and the radiation detection means can acquire the radiation tomography image. Therefore, the radiation tomography imaging can start the X-ray tomography by assuredly moving the radiation detection means within the possible imaging range by referring to the possible imaging range of the preliminarily calculated possible imaging range of the radiation detection means. Accordingly, an incident in which the radiation source moves out of the movable range of the radiation source and interferes the floor or an incident in which the radiation imaging is suspended by predicting the inference of the radiation source can be absolutely avoided. As results, the laborious works and the time wasting for re-imaging can be prevented, so that a radiation tomography image having a high quality can be imaged adequately and efficiently.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 3 is a schematic view illustrating a calculation method of the FPD possible imaging range the detector position calculation means according to the aspect of the Embodiment 1.

FIG. 3A is illustrating a calculation method for a height of the X-ray focus point based on a height of the center point, an imaging distance, and an irradiation swing angle and FIG. 3B is illustrating a calculation method for a possible imaging range of the FPD based on a movable range of the X-ray tube, the imaging distance and irradiation swing angle.

FIG. 7A is illustrating tilting in the x-direction of the X-ray tube support element, FIG. 7B is illustrating the X-ray tube moving in a y-direction and tilting in the y-direction.

FIG. 16A, 16B are views illustrating a region of which all X-ray images can be generated so as to reconstruct the X-ray tomography image according to a radiation tomography device.

FIG. 16A is illustrating a structure of the radiation tomography imaging by fixing a position of the FPD according to the aspect of the Embodiment 1.

FIG. 16B is illustrating a structure of the radiation tomography imaging while the FPD and the X-ray tube are synchronously moving in the opposite direction each other according to the aspect of the Embodiment 2.

FIG. 17A is a schematic view illustrating an imaging preparation position and an imaging ending position.

FIG. 17B is a graph illustrating a change of the moving velocity of the X-ray tube.

FIG. 20A is illustrating a structure of a radiation tomography imaging by fixing the position of the FPD according to the aspect of the Embodiment 1.

FIG. 20B is illustrating a structure of a radiation tomography imaging while the FPD and the X-ray tube are synchronously moving in the opposite direction each other according to the aspect of the Embodiment 2.

FIG. 22A is illustrating a case in which a cross section height is high.

FIG. 22B is illustrating a case in which the cross section height is low.

DETAILED DESCRIPTION OF THE PREFERRED EMBODIMENTS

Figure 1:
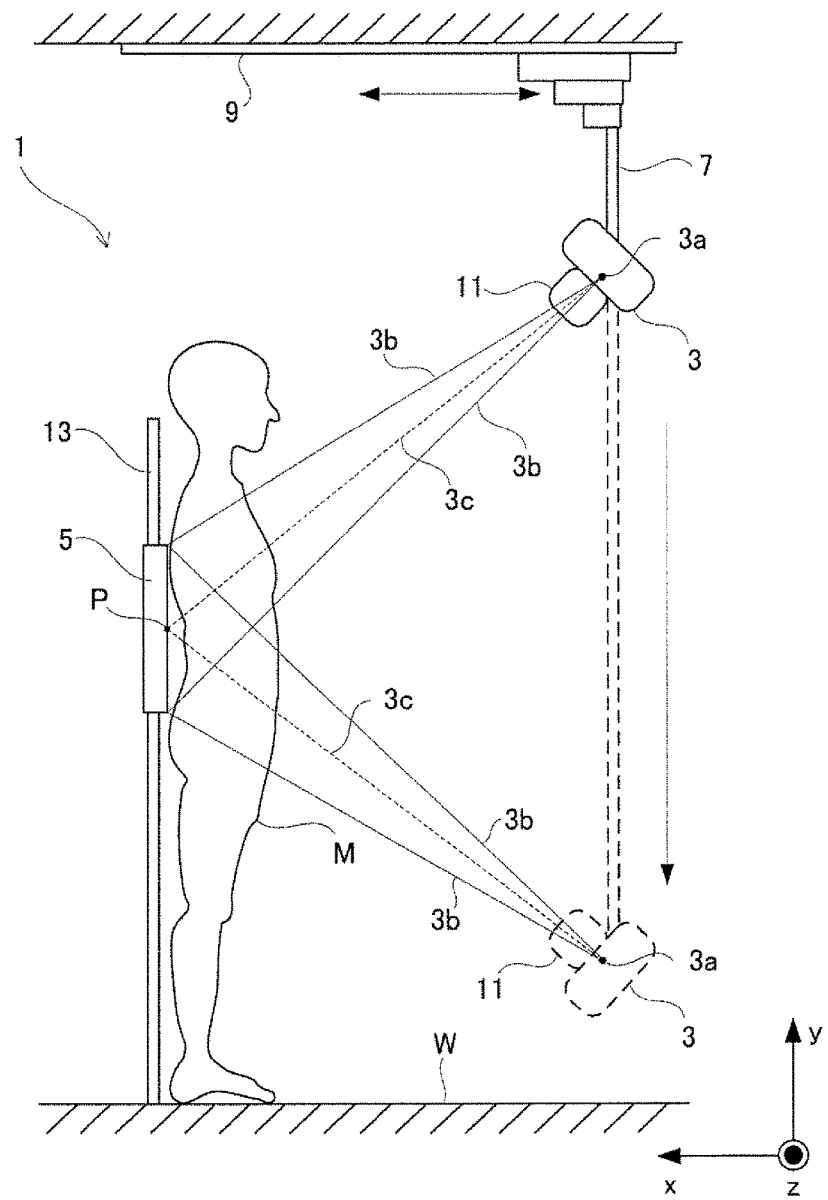
FIG. 1 is a schematic view illustrating a structure of a radiation tomography imaging device according to the aspect of the Embodiment 1.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Embodiment 1

Referring to FIGS., the inventor sets forth the Embodiment 1 of the present invention. In addition, the inventor sets forth using X-ray as an example of radiations.

(Illustration of the Entire Structure)

Referring to FIG. 1, the radiation tomography imaging device according to the aspect of the Embodiment 1 comprises an X-ray tube and an FPD 5 arranged facing each other as sandwiching the subject M. The X-ray tube 3 is supported by the X-ray tube supporting element 7 and irradiates the X-ray 3b from the X-ray focus 3a to the subject M. A base of the X-ray tube supporting element 7 is installed on the ceiling of the examination room and moves horizontally along with a rail 9 installed in the x-direction The collimator 11 installed to the X-ray tube 3 limits X-rays irradiated from the X-ray focus point 3a to a pyramid-like cone shape.

The FPD 5 is installed to the support post 13 vertically standing from the floor of the examination room so as to be movable freely up-and-down. The FPD 5 detects the X-ray 3b that is irradiated to the subject M from the X-ray focus point 3a and transmits there through, and converts to an electric signal there from and then outputs as an X-ray detection signal. The X-ray tube 3 corresponds to the radiation source of the present invention and the FPD 5 corresponds to the radiation detection means of the present invention.

Figure 2:
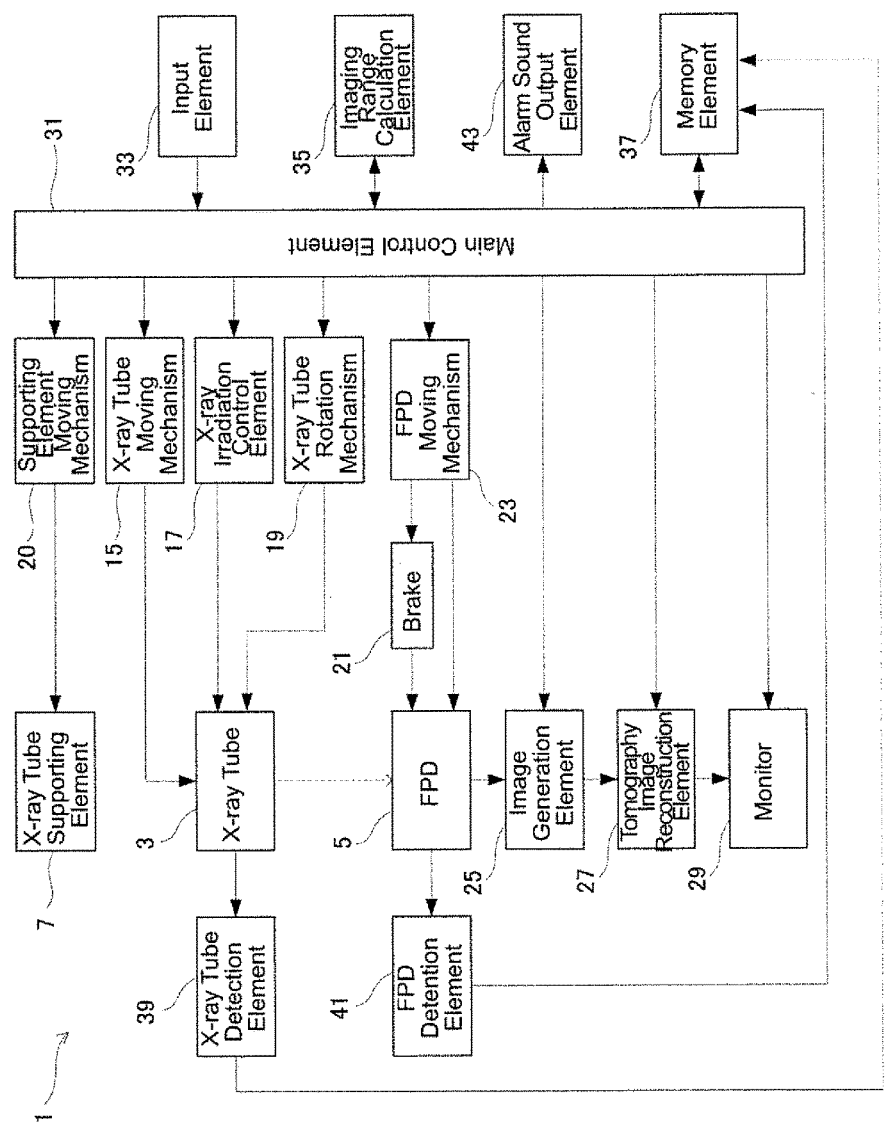
FIG. 2 is a functional block diagram illustrating the structure of the radiation tomography imaging device according to the aspect of the Embodiment 1.

In addition, referring to FIG. 2, an X-ray moving mechanism, an X-ray irradiation control element 17, and an X-ray tube rotation mechanism 19 are attached to the X-ray tube 3. The X-ray tube 3 is configured to move along the X-ray tube supporting element 7 in the y-direction, i.e., the body axis direction of the subject M according to the activation of the X-ray tube moving mechanism 15. In addition, the subject M is in a standing posture according to the aspect of the Embodiment, so that the X-ray tube moves in the vertical direction.

The X-ray irradiation control element 17 is configured to output a high voltage to the X-ray tube 3. Then, the amount of X-ray irradiated by the X-ray tube 3 and the timing of X-ray irradiation are controlled based on the high voltage output and the control signal provided by the X-ray irradiation control element 17. In addition, the X-ray tube 3 is configured to be rotatable around the axis in the z-direction by the X-ray tube rotation mechanism 19. Accordingly, the X-ray tube can change the irradiation angle without changing the own spatial position by the operation of the X-ray tube rotation mechanism 19. The X-ray tube moving mechanism 15 corresponds to a radiation source moving means of the present invention and the X-ray tube moving control element 17 corresponds to a radiation source moving control means of the present invention.

An X-ray supporting element moving mechanism 20 is attached to the X-ray supporting element 7. The X-ray supporting element moving mechanism 20 moves horizontally the X-ray tube supporting element 7 along a rail 9 in the x-direction. The X-ray tube is supported by the X-ray tube supporting element 7, so that the X-ray tube 3 moves horizontally in the x-direction along with moving of the X-ray tube supporting element 7.

A brake 21 and the FPD moving mechanism 23 are attached to the FPD 5. The brake 21 controls moving of the FPD 5 in the y-direction. The FPD moving mechanism 23 controls the brake 21 to be on-and-off. In addition, the FPD 5 is configured to move along the supporting post 12 in the y-direction according to the activation of the FPD moving mechanism 23.

The FPD 5 can be moved by the FPD moving mechanism 23 and additionally can be moved manually based on the structure thereof. Specifically, the operator can move manually the FPD 5 along the supporting post 13 in the y-direction after the brake 21 has been released. The FPD moving mechanism 23 corresponds to the detector moving means of the present invention.

An image generation element 25 is installed in the rear side of the FPD 5 and a tomography image reconstruction element 27 is installed in the rear side of the image generation element 25. The image generation element 25 generates the X-ray image of the subject M based on the X-ray detection signal output from the FPD 5. The tomography image reconstruction element 27 acquires the X-ray tomography image by reconstructing a plurality of X-ray images generated by the image generation element 25. A monitor 29 is connected to the tomography image reconstruction element 27 and the monitor 29 displays the X-ray tomography images reconstructed by the tomography image reconstruction element 27. The image generation element 25 corresponds to the image generation means of the present invention and the tomography image reconstruction element corresponds to the tomography image acquisition means of the present invention. In addition, the X-ray image corresponds to the radiation image of the present invention.

A main control element 31 comprehensively controls the X-ray tube moving mechanism 15, the X-ray irradiation control element 17, the X-ray tube rotation mechanism 19, the supporting element moving mechanism 20, the FPD moving mechanism 23, the image generation element 25, the tomography image reconstruction element 27 and the monitor 29. The input element 33 is a panel for the key-board input or a panel for the touch panel and the main control element 31 comprehensively controls according to the instruction input in the input element 33 by the operator. The main control element 31 corresponds to the detector moving control means of the present invention.

An imaging range calculation element 35 calculates the possible imaging range of the FPD 5 based on the parameters input to the input element 37 by the operator. The possible imaging range of the FPD 5 is the positional range of the FPD 5 in which the X-ray tomography images can be imaged without moving the moving region of the X-ray tube 3 to the outside of movable range of the X-ray tube 3. Meantime, the inventor sets forth the calculation method of the possible imaging range of the FPD 5 and the parameters to calculate the possible imaging range of the FPD 5 later.

A memory element stores the X-ray tomography imaging acquired by the tomography image reconstruction element 27 and the data of the possible imaging range of the FPD 5 calculated by the imaging range calculation element 35. The imaging range calculation element 35 corresponds to the imaging range calculation means of the present invention.

The radiation tomography imaging device according to the aspect of the Embodiment 1, the main control element 31 comprehensively controls the X-ray tube moving mechanism 15 and the X-ray tube rotation mechanism 19 so that the X-ray tube 3 can irradiate always the X-ray 3b toward the FPD 5. Specifically, referring to FIG. 1, the X-ray tube moving mechanism 15 moves the X-ray tube 3 from the position indicated by the solid line to the position indicated by the broken line in the y-direction and the X-ray rotation mechanism 19 tilts the X-ray tube 3 relative to the y-direction so that the center axis 3c of the X-ray 3b can pass always the center point P of the detection face of the FPD 5. The X-ray tube 3 changes sequentially an irradiation angle of the X-ray 3b interlockingly with the moving in the y-direction, so that the X-ray tube 3 can irradiate the X-ray 3b always toward the FPD 5.

Further, an X-ray tube detection element 39 is attached to the X-ray tube 3 and the FPD detection element 41 is attached to the FPD 5. The X-ray tube detection element 39 detects a moving distance in the y-direction of the X-ray tube 3 and the moving distance of the X-ray tube supporting element 7 in the x-direction, as needed. Then, the X-ray tube detection element 39 calculates the positional information of the X-ray tube 3 based on each detected moving distance, as needed.

The FPD detection element 41 detects a moving distance in the y-direction of the FPD 5, as needed. Then, the FPD detection element 41 calculates the positional information of the FPD 5 based on each detected moving distance, as needed. According to the aspect of the present Embodiment, both X-ray tube detection element 39 and the FPD detection element 41 are potentiometers, but an encoder instead of potentiometer can be employed. The positional information of the X-ray tube 3 calculated by the X-ray tube detection element 39 and the positional information of the FPD 5 calculated by the detection element 41 are stored in the memory element 37, as needed.

The radiation tomography imaging device 1 further comprises an alarm sound output element 43. The positional information of the FPD 5 calculated by the detection element 41 and the information of the possible imaging range of the FPD 5 are sent to the alarm sound output element 43 through the main control element 31, as needed. The alarm sound output element 43 is configured to output an alarm sound when the current position of the FPD 5 is out of the possible imaging range of the FPD 5. An example of the alarm sound can be buzzer sounds or voices.

(According to the Aspect of the Embodiment 1, an Calculation Method of the Possible Imaging Range of the FPD)

Here, the inventor sets forth the method how the imaging range calculation element 35 can calculate the possible imaging range of the FPD 5.

Further, referring to FIG. 3A, when the X-ray tomography imaging is conducted, the position of the X-ray focus point 3a, at which the X-ray is first irradiated from the X-ray tube 3, is specified as a "irradiation start position" and indicated by the sign A. When the X-ray tomography imaging is conducted, the position of the X-ray focus point 3a, at which the X-ray is last irradiated from the X-ray tube 3, is specified as a "irradiation end position' and indicated by the sign B. Specifically, the straight line AB is the moving region of the X-ray tube 3, i.e., the moving range of the X-ray focus point 3a when the X-ray tomography imaging is conducted. Hereinafter, the inventor sets forth the moving region of the X-ray tube 3 as indicated by the sign J.

And the distance between the X-ray focus point 3a and the detection face of the FPD 5 is specified (hereinafter "imaging distance") and indicated by the sign G. The imaging distance G corresponds to i.e., the distance between the focus point and the receiving face (SID: Source Image Distance.) A swing angle of the X-ray tube 3 from the irradiation start position A to the irradiation end position B (hereinafter, "irradiation swing angle"), i.e., the degree of ∠APB is θ. When the X-ray is irradiated and given the center point of the detection face of the FPD 5 is fixed, a height from the floor surface W 69 to the center point P is a height F.

Here, an intersection of the normal line the detection face of the FPD 5 passing the center point P and the straight line AB is C. According to the imaging of the X-ray tomography image, the X-ray tube 3 moves while the respective angle ∠APC and ∠BPC are being equal. Accordingly, either degree of ∠APC or ∠BPC is θ/2. Further, the straight line AB is parallel in the y-direction, so that the straight line PC and the straight line AB are orthogonal. The length of the straight line PC is equal to the length G of the imaging distance, so that the length $D_{AC}$ of the straight line AC and the length $D_{BC}$ of the straight line BC are calculated using the following formula (1).

$$D_{AC}=D_{BC}=G \tan(\theta/2) \quad (1)$$

And, if the height from the floor surface W to the irradiation start position A is Sa and a height from the floor surface W to the irradiation end position is Sb, the below two formulae are completed.

$$Sa=F+D_{AC}=F+G \tan(\theta/2) \quad (2)$$

$$Sb=F-D_{BC}=F-G \tan(\theta/2) \quad (3)$$

Here, the movable range of the X-ray tube 3 is preset depending on the mechanical limitation of the radiation tomography imaging device. Accordingly, if a height of the floor surface W to the X-ray focus point 3a is S, the maximum $S_{max}$ of the height S and the minimum $S_{min}$ are specified values and the data of $S_{max}$ and min are stored in the memory element 37. Further, the movable range of the X-ray tube 3 specified by $S_{max}$ and $S_{min}$ is hereafter indicated as the sign SP.

And, when the moving region J of the X-ray tube 3 is going out of the movable range SP of the X-ray tube 3, the X-ray tube 3 moves to out of the movable range SP during the X-ray tomography imaging, and then the X-ray tube 3 may be interfered by the floor surface. Accordingly, the moving region J of the X-ray tube 3 must be within the range of the movable range SP. Specifically, the height Sa of the irradiation start position A is never beyond the maximum $S_{max}$ and the height Sb of the irradiation end position B is never lower than the $S_{min}$, so that the formulas $S_{max} \geq Sa$ and $S_{min} \leq Sb$ are completed. Accordingly, the range of the height F from the floor surface W to the center point P of detection face can be calculated using the below formula (4).

$$S_{max}-G\tan(\theta/2) \geq F \geq S_{min}+G\tan(\theta/2) \quad (4)$$

Therefore, the imaging range calculation element 35 calculates the range of the height F from the floor surface W to the center point P of the FPD 5 by using the imaging distance G, the irradiation swing angle θ, the maximum $S_{max}$ of the height S and the minimum $S_{min}$ of the height S. Further, the maximum of the height F calculated by the above formula (4), i.e., $S_{max}-G\tan(\theta/2)$ is specified as $F_{max}$. And the minimum of the height F calculated by the above formula (4), i.e., $S_{min}+G\tan(\theta/2)$ is specified as $F_{min}$.

The possible imaging range of the FPD 5 can be calculated by using $F_{max}$ and $F_{min}$. Specifically, referring to FIG. 3B, if $Sa=S_{max}$ is completed, the height F of the center point P is the maximum $F_{max}$. In such case, the position of the center point P of the detection face of the FPD 5 is indicated by the sign P1. And if $Sb=S_{min}$ is completed, the height F of the center point P is $F_{min}$. In such case, the position of the center point P is indicated by the sign P2.

When the center point of the FPD 5 is positioned on the straight line $P_1 P_2$, the moving region J of the X-ray tube 3 must be within the range of the movable range SP. In such case, when the X-ray tomography imaging is conducted, the X-ray tube 3 is never going out of the movable range SP. Specifically, when the center point of the FPD 5 is positioned on the straight line $P_1 P_2$, the possible imaging range of the FPD 5 is the range where the FPD 5 is in place.

Here, if the length from the center point P to the upper end of the FPD 5 and the length from the center point P to the lower end of the FPD 5 is R, the maximum of the height from the floor surface W to the upper end of the FPD 5 is ($F_{max}+R$.) And the minimum of the height from the floor surface W to the lower end of the FPD 5 is ($F_{min}-R$.) The length of R is predetermined value based on the size of the FPD 5. Accordingly, the possible imaging range of the FPD 5 is specified by using $F_{max}$, $F_{min}$ and R. Further, the possible imaging range of the FPD 5, specified by $F_{max}$, $F_{min}$ and R, is hereafter indicated as the sign FP.

The imaging distance G and the irradiation swing angle θ are any parameters that the operator determines preliminarily and arbitrarily in accordance with a cross section thickness, an enlargement factor and so forth of the X-ray tomography image. And $S_{max}$ and $S_{min}$ are predetermined parameters in accordance with a specification of the radiation tomography imaging device 1. Accordingly, the operator preliminarily can calculate the possible imaging range FP of the FPD 5 prior to start of moving the X-ray tube 3 and can conduct the X-ray tomography imaging under the situation in which the FPD 5 is certainly within the range of the possible imaging range FP of the FPD 5. As results, the moving of the X-ray tube 3 out of the movable range SP when the X-ray tomography imaging is conducted can be avoided, so that the imaging of the X-ray tomography imaging can be performed adequately.

(Operation According to the Aspect of the Embodiment 1)

Figure 4:
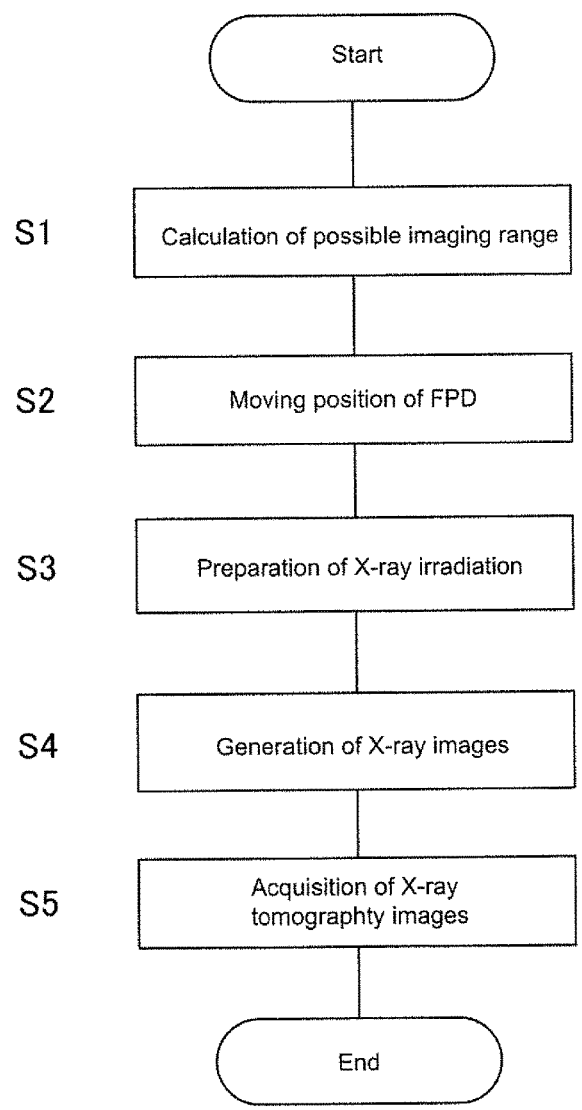
FIG. 4 is a flow chart illustrating operational steps of the radiation tomography imaging device according to the aspect of the Embodiment 1.

Next, the inventor sets forth the operation of the radiation tomography imaging device 1 according to the aspect of the Embodiment 1. FIG. 4 is a flow chart illustrating operational steps of the radiation tomography imaging device according to the aspect of the Embodiment 1. Further, referring to FIG. 5, the radiation tomography imaging device 1 according to the aspect of the Embodiment 1, the subject M is in the standing posture and referring to FIG. 5, the X-ray tube 3 and the FPD 5 are in the position indicated by the solid line.

Step S1 (Calculation of the Possible Imaging Range)

First, the operator calculates a possible imaging range of the FPD 5. Specifically, the operator inputs parameters related to the imaging distance G and the irradiation swing angle θ by operating the input element 33. Each input parameter is sent to the imaging range calculation element 35. In addition, the memory element 37 stores the maximum $S_{max}$ of the height S from the floor surface W to the X-ray focus point 3a and the minimum $S_{min}$ of the height S. And parameters of the maximum $S_{max}$ and the minimum $S_{min}$ are sent to the imaging range calculation element 35 from the memory element 37.

Figure 5:
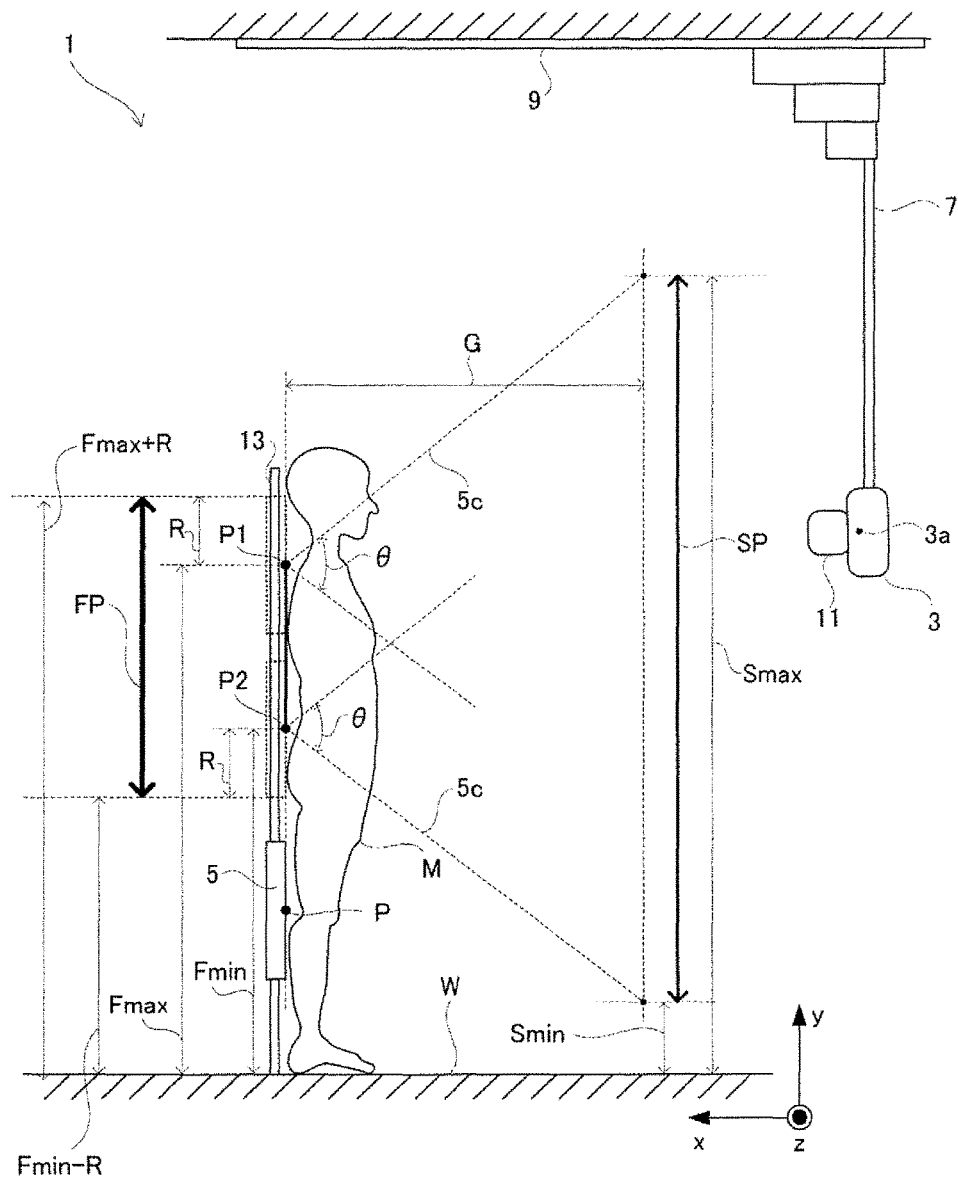
FIG. 5 is a schematic view illustrating a step S1 relative to a radiation tomography imaging device according to the aspect of the Embodiment 1.

The imaging range calculation element 35 calculates the maximum $S_{max}$ and the minimum $S_{min}$ relative to the height of F from the floor surface to the center point of the detection face of the FPD 5 based on the received parameters, i.e., G, θ, $S_{max}$, and $S_{min}$. The length from the center point P of the FPD 5 to the upper end of the FPD 5 and the length from the center point P of the FPD 5 to the lower end of the FPD 5 is R. Referring to FIG. 5, the possible imaging range FP of the FPD 5 is specified as the range between the upper limit ($F_{max}$+R) and the lower limit ($F_{min}$−R) by using $F_{max}$, $F_{min}$ and R.

When the height F is $F_{max}$, the position of the center point is specified as P1 and when the height F is $F_{min}$, the position of the center point is specified as P2. When the FPD is in place in the range of the possible imaging range FP of the FPD 5, the center point P of the detection face of the FPD 5 is positioned on the straight line $P_1P_2$. And when the center point P is positioned on the straight line $P_1P_2$, the x-ray tube never moves out of the movable range SP under the conditions of the imaging distance G and the irradiation swing angle θ while the X-ray tomography imaging. Therefore the possible imaging range FP of the FPD 5, in which an adequate X-ray tomography image can be imaged adequately under the conditions of the imaging distance G and the irradiation swing angle θ, can be calculated.

Further, the operator may input the parameter only related to the irradiation swing angle θ without inputting the parameter related to the imaging distance G into the input element 33. In such case, the current positional information of the X-ray tube 3 calculated by the X-ray tube detection element 39 and the current positional information of the FPD 5 calculated by the FPD detection element 41 are respectively sent to the imaging range calculation element 35 from the memory element 37. The imaging range calculation element 35 calculates the distance from the X-ray focus point 3a to the detection face of the FPD 5 as the imaging distance G at the present time based on the received respective positional information. Then, the imaging range calculation element 35 calculates the movable range FP of the FPD 5 by using the calculated imaging distance G.

Step S2 (Moving the Position of the FPD 5)

Figure 6:
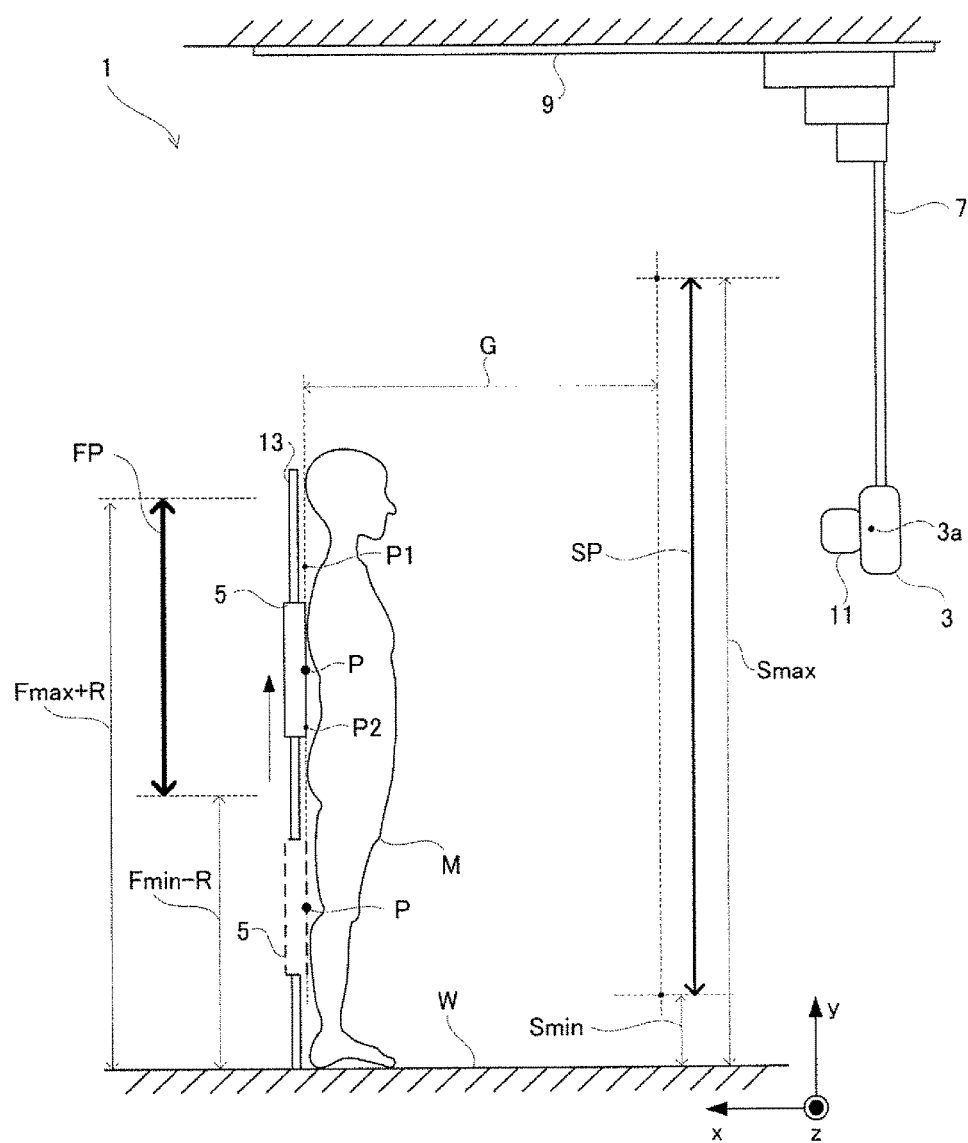
FIG. 6 is a schematic view illustrating the step S2 relative to a radiation tomography imaging device according to the aspect of the Embodiment 1.

Following the calculation of the possible imaging range of the FPD 5 by the imaging range calculation element 35, the position of the FPD 5 is moved, And first of all, the operator moves to the FPD 5 side to turn off therefor by operating the brake 21. The brake becomes off so that the FPD 5 becomes movable up-and-down in the y-direction along the supporting post 13. And referring to FIG. 6, the operator manually moves the FPD 5 from the position indicated by the broken line to the position indicated by the solid line corresponding to the position of the target region of the subject M.

Here, the positional information of the FPD 5 calculated by the detection element 41 and the information of the movable range of the FPD 5 calculated by the imaging range calculation element 35 are sent to the alarm sound output element 43, as needed. And, when the position of the FPD 5 is out of the possible imaging range FP, i.e., the center point P is not positioned on the straight line $P_1P_2$, the alarm sound output element 43 outputs alarm sounds. The operator can make sure the position of the FPD 5 is out of the possible imaging range FP due to the alarm sounds output from the alarm sound output element 43.

If the position of the FPD 5 is out of the possible imaging range FP, an adequate X-ray tomography imaging under the condition of the parameters of the imaging distance G and the irradiation swing angle θ cannot be conducted. Accordingly, the operator can quickly take measures to conduct an adequate X-ray tomography imaging corresponding to the received alarm sounds. For an example measures, the operator may move the FPD 5 in the range of the possible imaging range FP or newly input the parameters of the imaging distance G and the irradiation swing angle θ into the input element 33, but not limited thereto. When no alarm sounds are output from the alarm sound output element 43, the operator can make sure the position of the FPD 5 is in the range of the possible imaging range FP. Once the operator could make sure the position of the FPD 5 is in the range of the possible imaging range FP, the operator activates the brake 21 on to fix the position of the FPD 5.

Step S3 (Preparation of X-Ray Irradiation)

After moving the position of the FPD 5, next a preparation of the X-ray irradiation is conducted. Specifically, the operator inputs an instruction to prepare the X-ray irradiation by operating the input element 33. According to the instruction input into the input element 33, control signals are output from the main control element 31 to the X-ray tube moving mechanism, the X-ray rotation mechanism 19 and the supporting element moving mechanism 20.

Figure 7A:
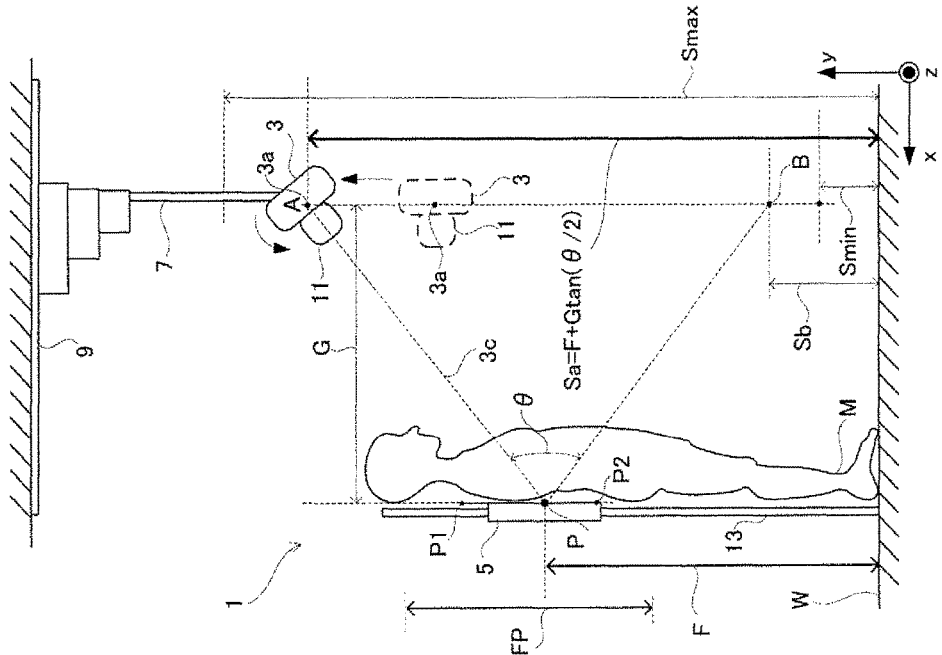
FIG. 7A, 7B are schematic views illustrating the step S3 relative to a radiation tomography imaging device according to the aspect of the Embodiment 1.

Referring to FIG. 7A, the supporting element moving mechanism 20 moves the X-ray tube supporting element 7 in the x-direction from the position indicated by the broken line to the position indicated by the solid line based on the given control signals. The X-ray tube 3 is supported by the X-ray tube supporting element 7, so that the X-ray tube 3 moves in the x-direction following the X-ray tube supporting element 7. The position, indicated by the solid line, of the X-ray tube supporting element 7 is the position at which the distance from the X-ray focus point 3a to the detection face of the FPD 5, i.e., the length of the imaging distance is G.

Figure 7B:
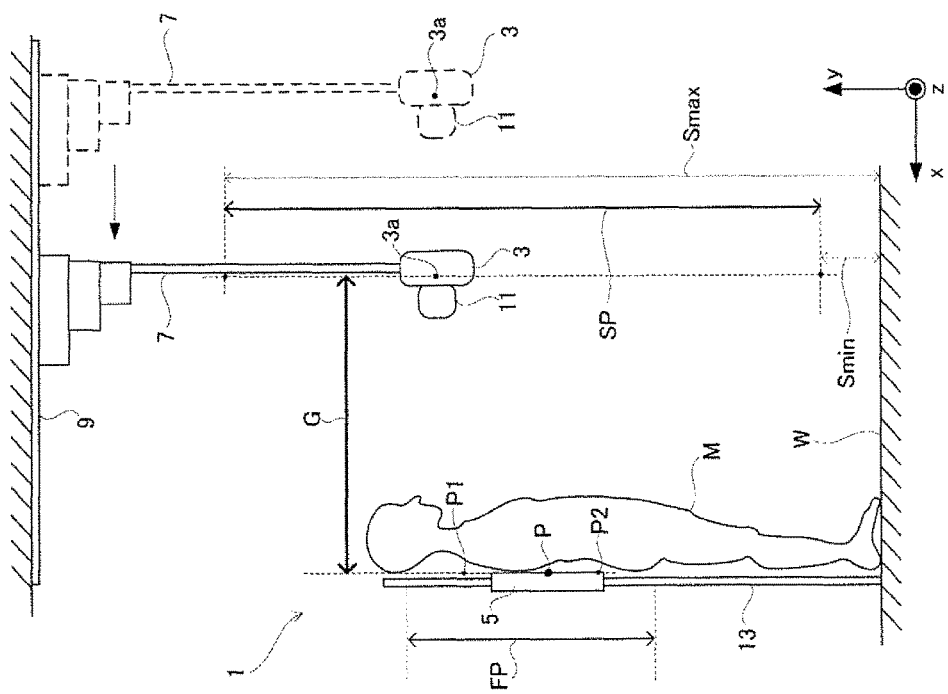

Referring to FIG. 7B, the X-ray tube moving mechanism 15 moves the X-ray tube 3 in the y-direction from the position indicated by the broken line to the position indicated by the solid line in synchronism with moving of the X-ray tube 3 in the x-direction. Referring to FIG. 7B, the position of the X-ray focus point 3a of the X-ray tube 3 indicated by the solid line is hereinafter an "imaging preparation position." Further, according to the aspect of the Embodiment 1, the imaging preparation position coincides with the irradiation start position A. Specifically, if the height F from the floor surface W to the center point P, the imaging distance G and the irradiation swing angle θ are used, the height from the floor surface W to the imaging preparation position is (F+G tan (θ/2.)

Further, the X-ray tube moving mechanism 19 tilts the X-ray tube 3 relative to the y-direction in synchronism with moving of the X-ray tube 3 in the y-direction. At this time, the tilting angle of the X-ray tube 3 can be controlled so that the center axis 3*c* of the X-ray irradiated from the X-ray focus point 3*a* can pass the center point P of the detection face of the FPD 5. The X-ray tube 3 moves so that the position of the X-ray focus point 3*a* can be the imaging preparation position and the preparation of the X-ray irradiation can be completed.

Step S5 (Generation of an X-Ray Image)

Figure 8:
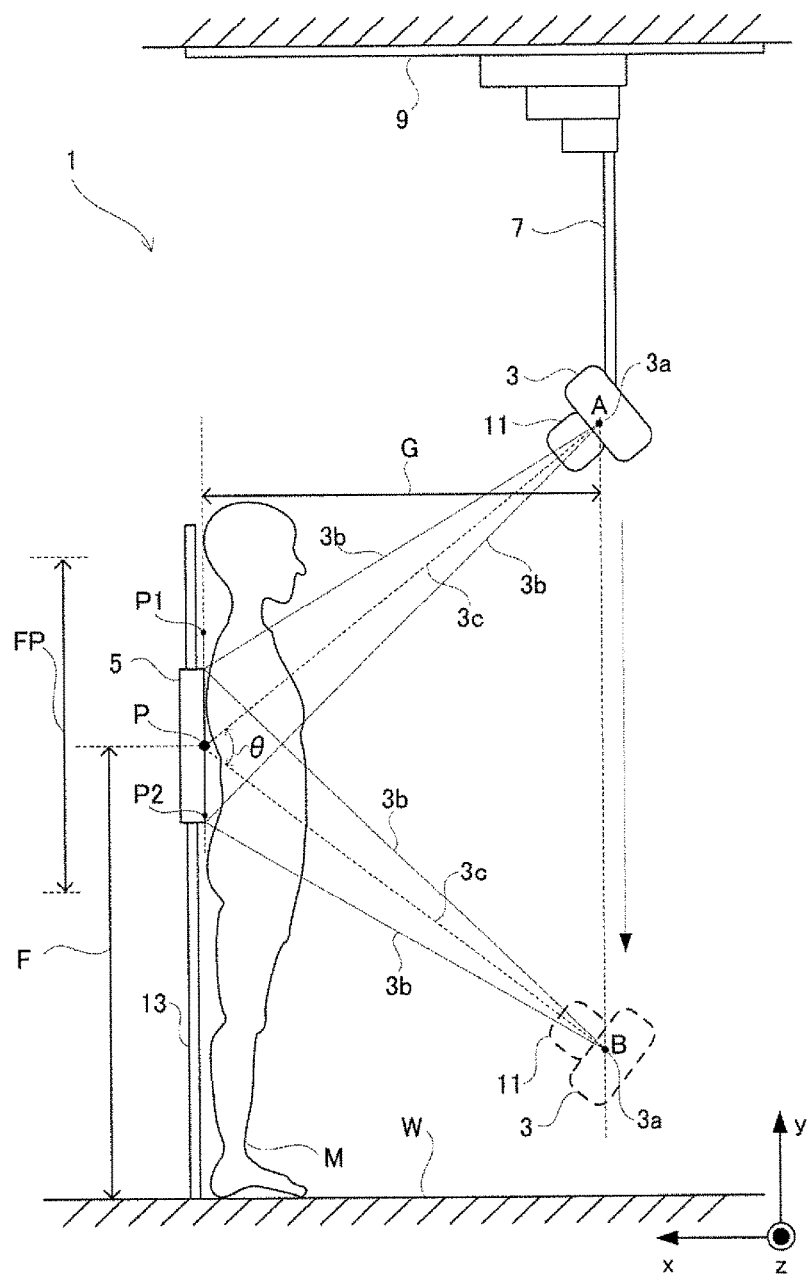
FIG. 8 is a schematic view illustrating the step S4 relative to a radiation tomography imaging device according to the aspect of the Embodiment 1.

Following the completion of the preparation of the X-ray irradiation, next an X-ray image is being generated. Specifically, the operator inputs an instruction to start the X-ray irradiation by operating the input element 33. According to the instruction input into the input element 33, control signals are output from the main control element 31 to the X-ray tube moving mechanism 15, the X-ray irradiation control element 17 and the X-ray rotation mechanism 19. The X-ray tube moving mechanism 15 moves the X-ray tube 3 in the straight line along the X-ray tube supporting element 7 in the y-direction based on the given control signals. Specifically, referring to FIG. 8, the X-ray focus point 3*a* is controlled so as to travel in the straight line from the irradiation start position A indicated by the solid line to the irradiation end position B indicated by the broken line.

The X-ray irradiation control element 17 irradiates the corn shaped X-ray 3*b* from the X-ray focus point 3*a* traveling in the straight line in the y-direction based on the output signals from the main control element 31. The irradiated X-ray 3*b* transmits the subject M and is being detected by the FPD 5. The FPD 5 that detects the X-ray 3*b* outputs the X-ray detection signals and the output X-ray detection signals are sent to the image generation element 25. The image generation element 25 generates X-ray images based on the received X-ray detection signals.

At this time, the X-ray rotation mechanism 19 tilts the X-ray tube 3 relative to the y-direction so that the center axis 3*c* of the X-ray 3*b* can pass always the center point P of the detection face of the FPD 5 in synchronism with moving of the X-ray tube 3 in the y-direction. Specifically, the X-ray rotation mechanism 19 rotates the X-ray tube 3 around the axis of the z-direction and controls the tilt angle of the X-ray tube 3 relative to y-direction based on the signals received from the main control element 31.

And the collimator 11 controls the shape of the X-ray 3*b* so that the X-ray 3*b* irradiated from the X-ray focus point 3*a* can be incident all over the detection face of the FPD 5. An irradiation angle of the X-ray 3*b* is changed sequentially and interlockingly with the moving of the X-ray tube 3 in the y-direction, so that the X-ray tube 3 can irradiate the X-ray 3*b* always toward the FPD 5.

In such way, while the X-ray tube 3 is moving in the y-direction from the irradiation start position A indicated by the solid line to the irradiation end position B indicated by the broken line, the X-ray 3*b* is irradiated intermittently from the X-ray focus point 3*a*. The number of irradiation times of the X-ray 3*b* is more than several ten times and, as one example, the X-ray 3*b* is irradiated 74 times. An X-ray image is generated every time when the X-ray 3*b* is irradiated, so that a series of the X-ray images imaged from respective different directions relative to the target region of the subject M can be generated every time when the X-ray tube 3 is moved in the y-direction. Once a series of X-ray images is generated, the data of the generated X-ray images are sent to the tomography image reconstruction element 27 from the image generation element 25. The X-ray tube 3 ends the X-ray irradiation at the position of the irradiation end position B and also suspends moving thereof in the y-direction.

Step S5 (Acquisition of an X-Ray Tomography Image)

Once a series of X-ray images is generated, the tomography image reconstruction element 27 reconstructs the data relative to the series of X-ray images. According to the reconstruction of image data relative to the X-ray image, an X-ray tomography image data of the subject M at the desired cross section position can be acquired. The monitor 29 displays the X-ray tomography images acquired by the tomography image reconstruction element 27. Further, according to the aspect of the Embodiment 1 a filter back projection method (FBP) is used as a method of reconstructing the image data, but instead, such as a shift addition method can also be used.

(Effects of a Configuration According to the Embodiment 1)

The radiation tomography imaging device 1 according to the aspect of the Embodiment 1 comprises the imaging distance calculation element 35. The imaging range calculation element 35 calculated the imaging distance G, the irradiation swing angle θ and the possible imaging range of the FPD 5 based on the movable range SP of the X-ray tube 3.

The imaging distance G and the irradiation swing angle θ are the parameters that the operator determines preliminarily and arbitrarily in accordance with a cross section thickness, an enlargement factor and so forth every time when an imaging of the X-ray tomography image is conducted. And the movable range SP of the X-ray tube 3 is a predetermined parameter relative to the radiation tomography imaging device 1. Accordingly, the operator can calculate preliminarily the possible imaging range FP of the FPD 5 prior to the start of moving the X-ray tube 3 by inputting the parameters of the imaging distance G and the irradiation swing angle θ into the input element 33.

The possible imaging range FP of the FPD 5 is the positional range of the FPD 5 in which the X-ray tomography images can be imaged without moving the moving region of the X-ray tube 3 to the outside of movable range of the X-ray tube 3. Accordingly, the operator starts moving the X-ray tube 3 while the FPD 5 is moved in the range of the possible imaging range of the FPD 5 referring to the preliminarily calculated possible imaging range FP, so that the X-ray tomography images can be imaged without letting the moving region J of the X-ray tube 3 move to the outside of the movable range SP of the X-ray tube 3.

On the other hand, according to the conventional radiation tomography imaging device, the possible imaging range of a FPD cannot be calculated. Therefore, the position of the FPD may be out of the possible imaging range of the FPD depending on the parameters of the height of the center point, the imaging distance, the irradiation swing angle and so forth. In such case, when a radiation tomography imaging is conducted, the X-ray tube moves outside of the movable range and may be interfered by the ceiling surface or the floor surface.

According to the conventional radiation tomography imaging device, e.g., an ultrasound sensor is installed to prevent the interference between an X-ray tube and a ceiling surface or floor surface or the like. The ultra sound sensor detects a possible interference between an X-ray tube and a ceiling surface or floor surface or the like and suspends moving of the X-ray tube based on a position or a moving velocity of the X-ray tube.

However, according to the conventional radiation tomography imaging device, such ultra sensor can only predict a possible interference between the X-ray tube and the floor surface or the like after the X-ray tube has started moving. Further, the step in which the X-ray tube starts moving corresponds to the step S3 according to the aspect of the Embodiment 1. Accordingly, the imaging of the X-ray tomography image can be suspended only after the X-ray tube has started moving. As results, the time and the labors for the operation prior to start of moving the X-ray tube would be wasteful. In addition, when the X-ray tomography imaging is suspended after the X-ray tube has started to irradiate the X-ray, a radiation must be re-irradiated to the subject M, so that an amount of the radiation exposure to the subject increases.

In contrast, the radiation tomography imaging device 1 according to the aspect of the Embodiment 1 calculates a possible imaging range FP of an FPD 5 at the step S1 in which an imaging distance or an irradiation swing angle is input into the input element 33. In the step S2, the operator moves from the place where the input element 33 is there to the side of the FPD 5 so as to change the position of FPD 5. At this time, a possible imaging range FP of the FPD 5 is already calculated, so that the operator can move assuredly the FPD 5 into the range of the possible imaging range of the FPD 5 referring to the possible imaging range FP.

And the operator moves again to the place where the input element is there from the side of the FPD 5 and inputs an instruction to prepare an X-ray tomography imaging (Step S3) and further operates the input element 33 to acquire the X-ray tomography image (Step S4, S5.) According to the aspect of the Embodiment 1, at the time of the step S3, the FPD 5 is certainly in place in the possible imaging range. Therefore, during the X-ray tomography imaging, an incident in which the X-ray tube is interfered by the floor surface and so forth, or an incident in which the X-ray tomography imaging is suspended in the middle thereof by sensing any possible interference with the X-ray tube 3 can be avoided.

When the X-ray tomography imaging is suspended at the later step of the step S3, the operator must re-input parameters of an imaging distance or an irradiation swing angle and must go-and-return between the place where the input element is set and the side of the FPD 5. Relative to the radiation tomography imaging device according to the aspect of the Embodiment, a suspension of an imaging after the step S3 and later can be avoided, so that the operator can conduct an imaging of the radiation tomography images without re-inputting and spending labors and time for go-and-return moving. In addition, the suspension of imaging after the X-ray tube 3 has started an X-ray irradiation can be avoided, so that the radiation exposure to the subject M can be suppressed relative to the X-ray tomography imaging.

Further, the radiation tomography imaging device 1 according to the aspect of the Embodiment 1 comprises an alarm sound output element 43, so that alarm sounds can be output when the position of the FPD 5 is out of the possible imaging range FP. Such alarm sounds can be structured with a buzzer or voice sounds. The operator hears the alarm sounds so that the operator can make sure the position of the FPD 5 is out of the possible imaging range FP. Accordingly, the operator can assuredly move the FPD 5 into the possible imaging range.

Embodiment 2

Next, referring to FIGS., the inventors set forth the Embodiment 2 of the present invention. In addition, the inventor skips the detail description of the structure that is the same as the structure of a radiation tomography imaging device 1 according to the aspect of the Embodiment 1 but marking the same reference sign.

(Characteristic Structure Relative to Embodiment 2)

Figure 9:
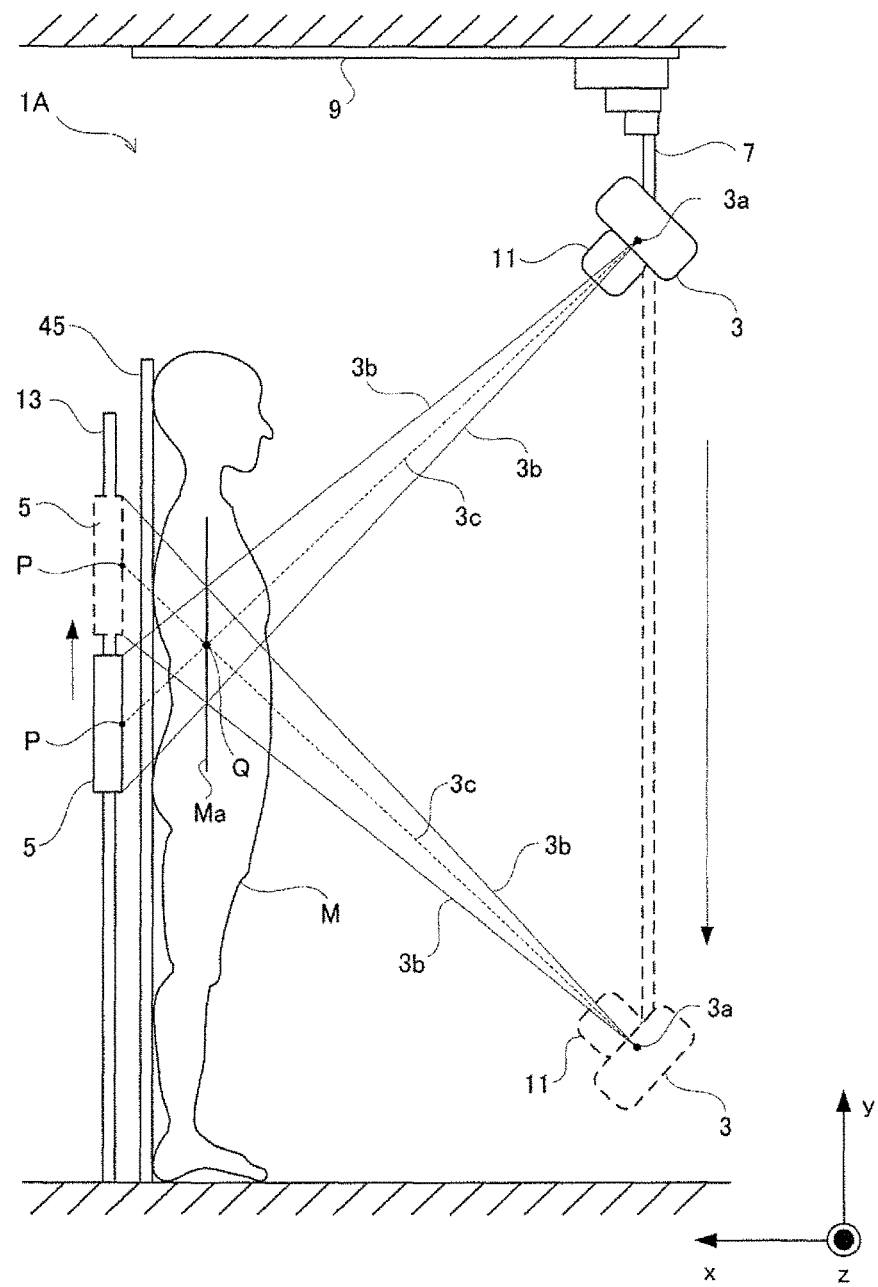
FIG. 9 is a schematic view illustrating a structure of a radiation tomography imaging device according to the aspect of the Embodiment 2.

The radiation tomography imaging device according to the aspect of the Embodiment 2, the main control element 31 comprehensively controls the X-ray tube moving mechanism 15 and the X-ray tube rotation mechanism 23 so that the X-ray tube 3 can move synchronously the FPD 5 during X-ray tomography imaging. Specifically, referring to FIG. 9, the X-ray tube moving mechanism 15 moves the X-ray tube 3 from the position indicated by the solid line to the position indicated by the broken line in the y-direction in the straight line and an FPD moving mechanism 23 moves the FPD 5 from the position indicated by the solid line to the position indicated by the broken line in the y-direction in the straight line. Thus, the X-ray tube 3 and the FPD 105 move in the opposite direction and in synchronism with each other, sandwiching the subject M while keeping the positions facing each other.

The X-ray rotation mechanism 19 tilts the X-ray tube 3 relative to the y-direction so that the center axis 3c of the X-ray 3b can pass always the tomography center Q. And the FPD moving mechanism 23 moves the FPD 5 in the y-direction so that the center axis 3c can pass always the center point P of the detention face of the FPD 5. The X-ray tube 3 changes sequentially an irradiation angle θ of the X-ray 3b interlockingly with moving in the y-direction, so that the X-ray tube 3 can irradiate intermittently the X-ray 3b always toward the FPD 5.

The image generation element 25 generates lots of X-ray images, relative to the reference tomographic section Ma which includes the tomography center Q and is a parallel section to the detection face of the FPD 5, based on the X-ray detection signals received from the FPD 5. The tomography image reconstruction element 27 reconstructs the X-ray image relative to the reference tomographic section Ma, so that the X-ray tomography images at a desired section can be acquired.

In addition, a partition 45 is installed between the subject M and the FPD 5. The partition 45 can keep stably the position of the subject M in a standing posture thereof and prevents interference between the subject M and the FPD 5 moving in the y-direction.

(According to the Aspect of the Embodiment 2, an Calculation Method of the Possible Imaging Range of the FPD)

Here, according to the aspect of the Embodiment 2, the inventor sets forth the method how the imaging range calculation element 35 can calculate the possible imaging range of the FPD 5.

Figure 10:
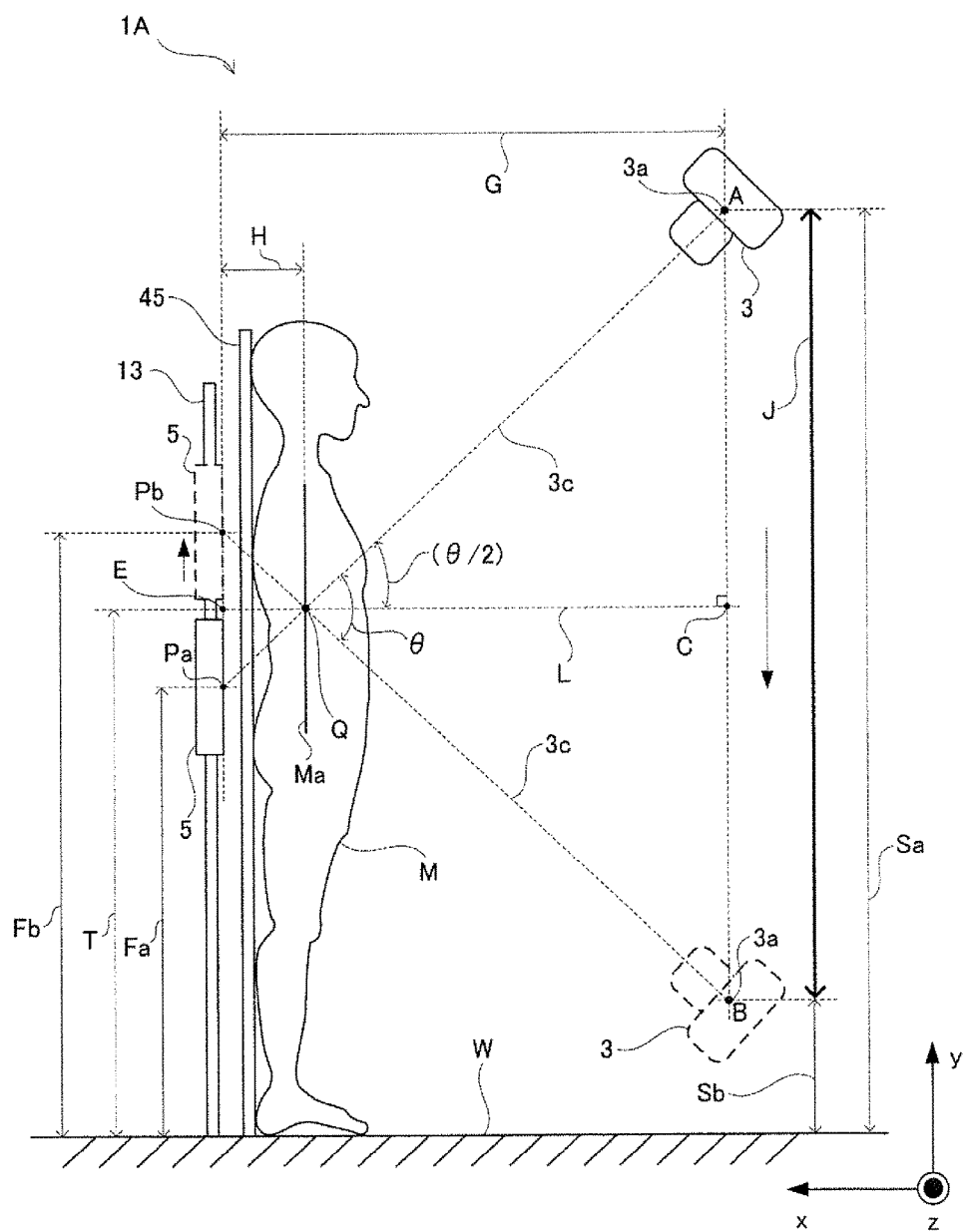
FIG. 10 is illustrating a calculation method for a height of the X-ray focus point based on a height of a target region, an imaging distance, an irradiation swing angle and a cross section height.

Further, referring to FIG. 10, according to the aspect of the Embodiment 2, the center axis 3c of the X-ray 3b irradiated from the X-ray focus point 3a passes always the tomography center Q. Therefore, according to the aspect of the Embodiment 2, the irradiation swing angle of the X-ray tube 3 relative to the X-ray tomography imaging is ∠AQB. Here, the degree of the irradiation swing angle is θ. And the distance from the tomography center Q to the detection face of the FPD 5 is H (hereafter tomographic section height).

In addition, when the X-ray focus point 3a is the position of the irradiation start position A, the position of the center point P of the detection face of the FPD 5 is a detection start position and indicated by the sign Pa. And when the X-ray focus point 3a is the position of the irradiation end position B, the position of the center point P of the detection face of the FPD 5 is a detection end position and indicated by the sign Pb. Specifically, the straight line PaPb is the moving region of the FPD 5, i.e., the moving range of the center point P of the detection face of the FPD 5 when the X-ray tomography imaging is conducted. Further, the height from the floor surface W to the detection start position Pa is Fa. And the height from the floor surface W to the detection end position Pb is Fb.

Here, the intersection of the normal L from the tomography center Q to the detection face of the FPD 5 and the straight line AB is C and the intersection of the normal L and the straight line PaPb is E. According to the imaging of the X-ray tomography image, the X-ray tube 3 moves while the respective angles ∠AQC and ∠BQC are being equal. Accordingly, either degree of ∠AQC or ∠BQC is ($\theta/2$.) Further, the straight line AB are parallel in the y-direction, so that the normal L and the straight line AB are orthogonal each other. The length of the straight line CE and the imaging distance G are equal each other and the length of the straight line EQ is equal to the height of the tomographic section height H, so that the length of the straight line CQ is (G−H.) Accordingly, the length $D_{AC}$ of the straight line AC and the length $D_{BC}$ of the straight line BC are calculated using the following formula (5).

$$D_{AC} = D_{BC} = (G-H)\tan(\theta/2) \quad (5)$$

And, the height from the floor surface W to the irradiation start position A is Sa and a height from the floor surface W to the irradiation end position B is Sb can be calculated by applying the height T from the floor surface W to the tomography center Q based on the below formulae (6) and (7).

$$Sa = T + D_{AC} = T + (G-H)\tan(\theta/2) \quad (6)$$

$$Sb = T - D_{BC} = T - (G-H)\tan(\theta/2) \quad (7)$$

Here, the moving region J of the X-ray tube 3 must be always within the range of the movable range SR Accordingly, the range of the height T from the floor surface W to the target region Q can be calculated using the below formula (11).

$$S_{max} - (G-H)\tan(\theta/2) \geq T \geq S_{min} + (G-H)\tan(\theta/2) \quad (8)$$

Therefore, the imaging range calculation element 35 calculates the range of the height T by using the imaging distance G, the irradiation swing angle $\theta$, the tomographic section height H, the maximum $S_{max}$ of the height S and the minimum $S_{min}$ of the height S. Further, the maximum of the height T calculated by the above formula (8), i.e., $S_{max} - (G-H)\tan(\theta/2)$ is specified as $T_{max}$. And, the minimum of the height F calculated by the above formula (8), i.e., $S_{min} + (G-H)\tan(\theta/2)$ is specified as $T_{min}$.

The range of the position of the tomography center Q can be calculated based on $T_{max}$ and $T_{min}$ so that the moving region J of the X-ray tube 3 can be in the range of the movable range of the X-ray tube 3. Specifically, referring to FIG. 11, if $Sa = S_{max}$ is completed, the height T of the tomography center Q is the maximum $T_{max}$. In such case, the position of the tomography center Q is indicated by the sign $Q_1$. And if $Sb = S_{min}$ is completed, the height T of the tomography center Q is $T_{min}$. In such case, the position of the tomography center Q is indicated by the sign $Q_2$. Specifically, when the tomography center Q is positioned on the straight line $Q_1 Q_2$, the moving region J of the X-ray tube 3 must be always within the range of the movable range SP of the X-ray tube 3.

As described later, the operator moves the FPD 5 corresponding to the target region of the subject M in the step S2. And the position of the tomography center Q is calculated based on the position of the center point P of the detection face of the FPD 5. Specifically, the position of the tomography center Q is determined so that the height F of the center point P after the FPD 5 has moved can be equal to the height T from the floor surface W to the tomography center Q. Accordingly, the possible imaging range FP of the FPD 5 can be calculated by using the $T_{max}$ and the $T_{min}$.

Figure 11:
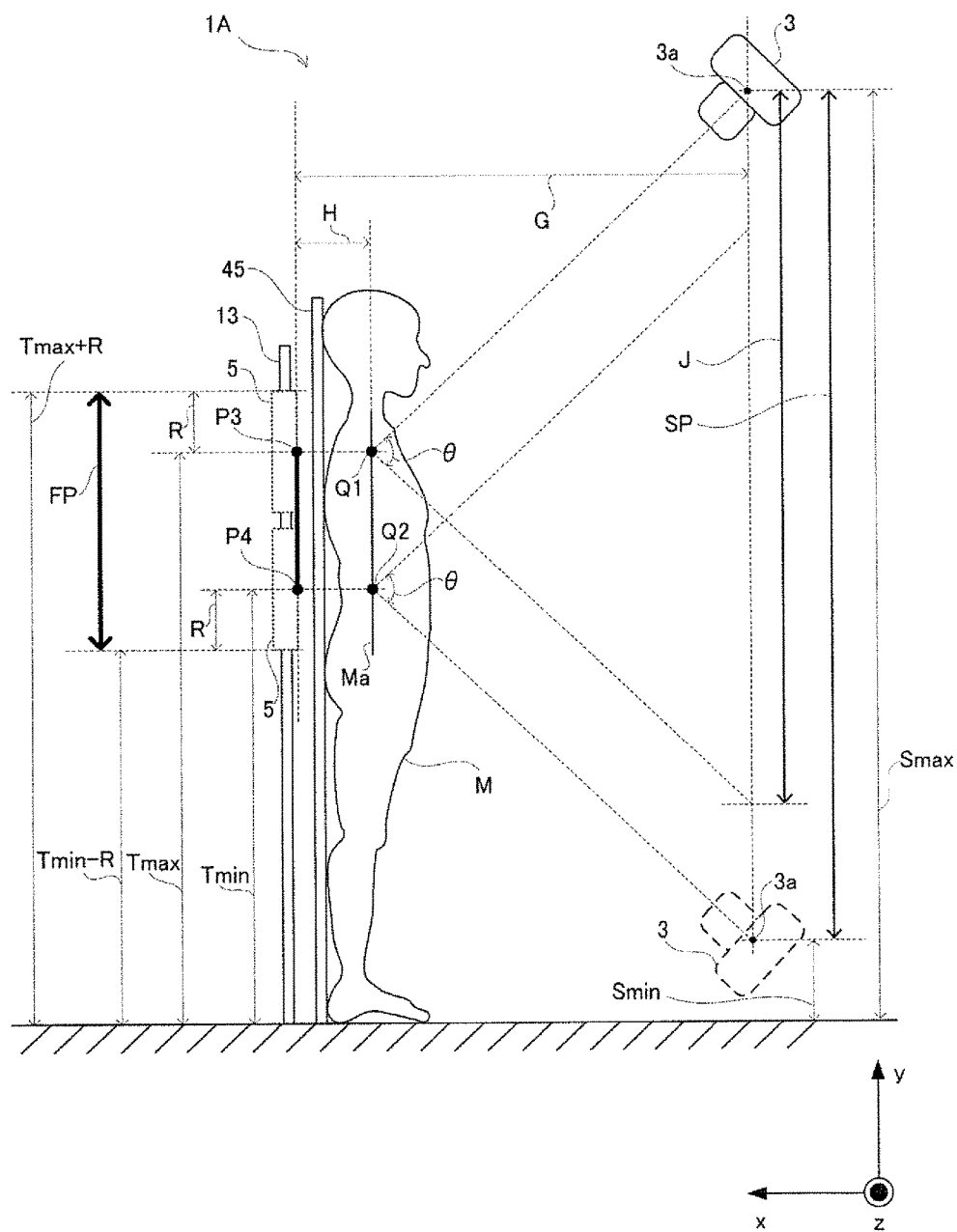
FIG. 11 is illustrating a calculation method for a possible imaging range of the FPD based on a movable range of the X-ray tube, an imaging distance, an irradiation swing angle and a cross section height.

Specifically, referring to FIG. 11, if $F = T_{max}$ is completed, the height F becomes the maximum. In such case, the position of the center point P is indicated by the sign P3. And if $F = T_{min}$ is completed, the height F becomes the minimum. In such case, the position of the center point P is indicated by the sign P4.

The FPD 5 is moved corresponding to the target region of the subject M, so that the tomography center Q is positioned on the straight line $Q_1 Q_2$ when the center point P is positioned on the straight line P3P4. When the X-ray tomography imaging is conducted, the moving region J of the X-ray tube 3 is within the range of the movable range SP of the X-ray tube 3. Specifically, when the center point P of the FPD 5 is positioned on the straight line $P_3 P_4$, the possible imaging range of the FPD 5 is the range where the FPD 5 is in place.

Here, if the length from the center point P to the upper end of the FPD 5 is R, the upper limit of the possible imaging range FP is where the height F is ($T_{max} + R$.) And the lower limit of the possible imaging range FP is where the height F is ($T_{min} - R$.) The length of R is predetermined value based on the size of the FPD 5. Accordingly, the possible imaging range FP of the FPD 5 can be determined by using $T_{max}$, $T_{min}$ and R.

Therefore, the imaging range calculation element 35 calculates the possible imaging range FP of the FPD 5 by using the imaging distance G, the irradiation swing angle $\theta$, the tomographic section height H, the maximum $S_{max}$ of the height S and the minimum $S_{min}$ of the height S. The tomographic section height H is the distance between the tomography center Q corresponding to the target region of the subject M and the detection face of the FPD 5. Accordingly, the tomographic section height H is a parameter determined arbitrarily by an operator prior to an X-ray tomography imaging according to a distance between the detection face of the FPD 5 and the partition 45, the body size of the subject M and so forth. Accordingly, the operator preliminarily can calculate the possible imaging range FP of the FPD 5 prior to start of moving the X-ray tube 3 and can conduct the X-ray tomography imaging under the situation in which the FPD 5 is certainly within the range of the possible imaging range FP of the FPD 5.

In addition, the height Fa from the floor surface W to the detection start position Pa and the height Fb from the floor surface W to the detection end position Pb can be calculated also using the tomographic section height H and the swing angle $\theta$. The length of the straight line EQ is equal to the tomographic section height H. Accordingly, either degree of ∠EQPa or ∠EQPb is ($\theta/2$.) Accordingly, the length $D_{EPa}$ of the straight line EPa and the length $D_{EPb}$ of the straight line EPb are calculated using the following formula (9).

$$D_{EPa} = D_{EPb} = H\tan(\theta/2) \quad (9)$$

And, a height Fa from the floor surface W to the detection start position Pa and a height from the floor surface W to the detection end position Pb can be calculated by applying the height T from the floor surface W to the tomography center Q based on the below formulae (10) and (11).

$$Fa = T - D_{EPa} = T - H \tan(\theta/2) \qquad (10)$$

$$Fb = T + D_{EPb} = T + H \tan(\theta/2) \qquad (11)$$

(Operation According to the Aspect of the Embodiment 2)

Figure 12:
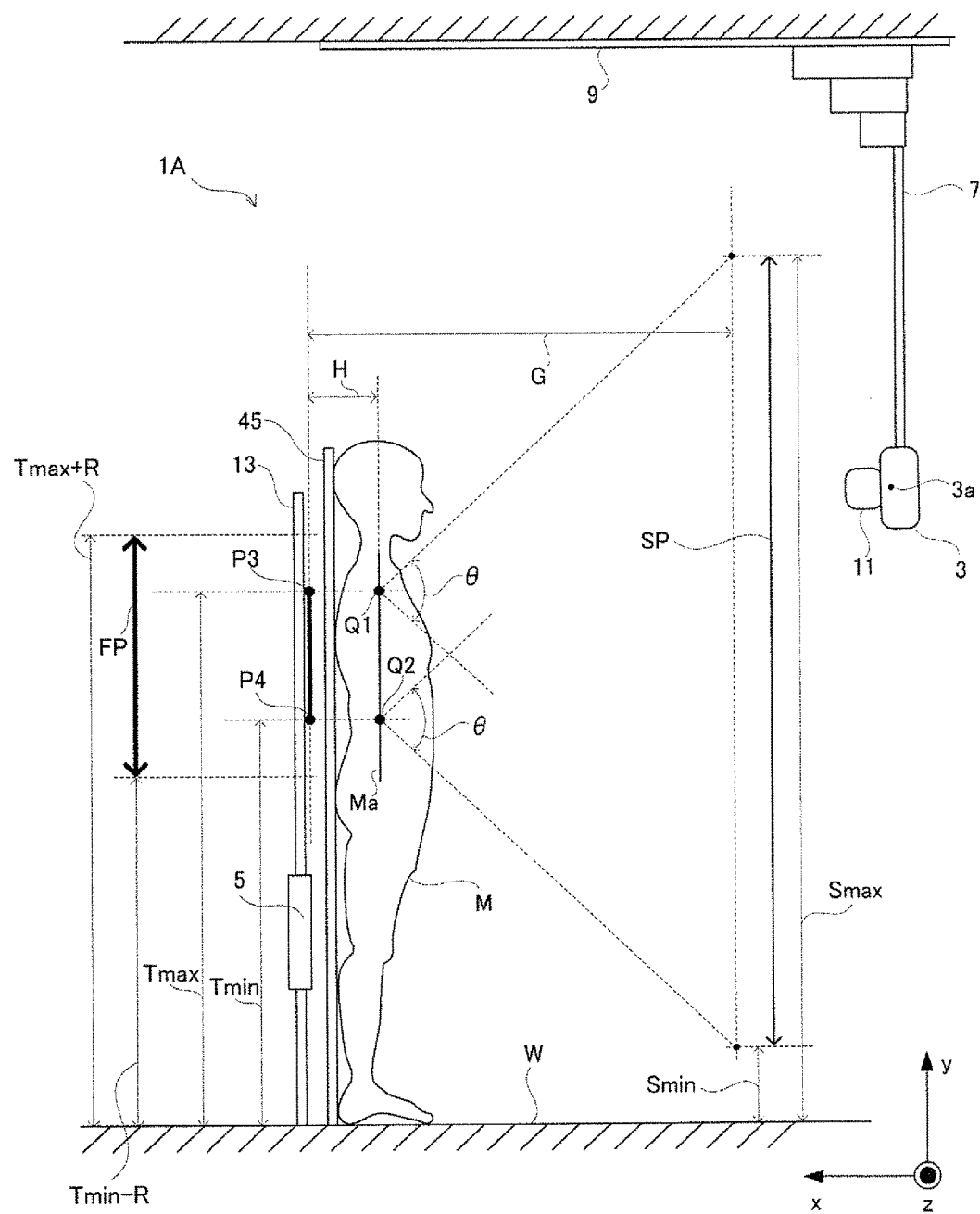
FIG. 12 is a schematic view illustrating a step S1 relative to a radiation tomography imaging device according to the aspect of the Embodiment 2.

Next, the inventor sets forth the operation of the radiation tomography imaging device 1A according to the aspect of the Embodiment 2. A flow chart illustrating operational steps of the radiation tomography imaging device according to the aspect of the Embodiment 2 is the same as the flow chart according to the aspect of the Embodiment 1. Further, referring to FIG. 12, the X-ray tube 3 and the FPD 5 are supposed in the position indicated by the solid line.

Step S1 (Calculation of the Possible Imaging Range)

First, the operator calculates a possible imaging range of the FPD 5. Specifically, the operator inputs parameters related to the imaging distance G, the irradiation swing angle θ and the tomographic section height H by operating the input element 33. Each input parameter is sent to the imaging range calculation element 35. In addition, the parameters of the maximum $S_{max}$ of the height S from the floor surface W to the X-ray focus point 3a and the minimum $S_{min}$ of the height S are sent to the imaging range calculation element 35 from the memory element 37.

The imaging range calculation element 35 calculates the maximum $S_{max}$ and the minimum $S_{min}$ relative to the height of T from the floor surface W to the tomography center Q based on the received parameters, i.e., G, θ, $S_{max}$, and $S_{min}$. At this time, the upper limit value ($T_{max}$+R) and the lower limit value ($T_{min}$−R) of the possible imaging range FP are calculated using $T_{max}$, $T_{min}$ and the constant R. Therefore, the possible imaging range FP of the FPD 5, in which an adequate X-ray tomography image can be imaged under the conditions of the imaging distance G and the irradiation swing angle θ and the tomographic section height H can be calculated.

Step S2 (Moving the Position of the FPD 5)

Figure 13:
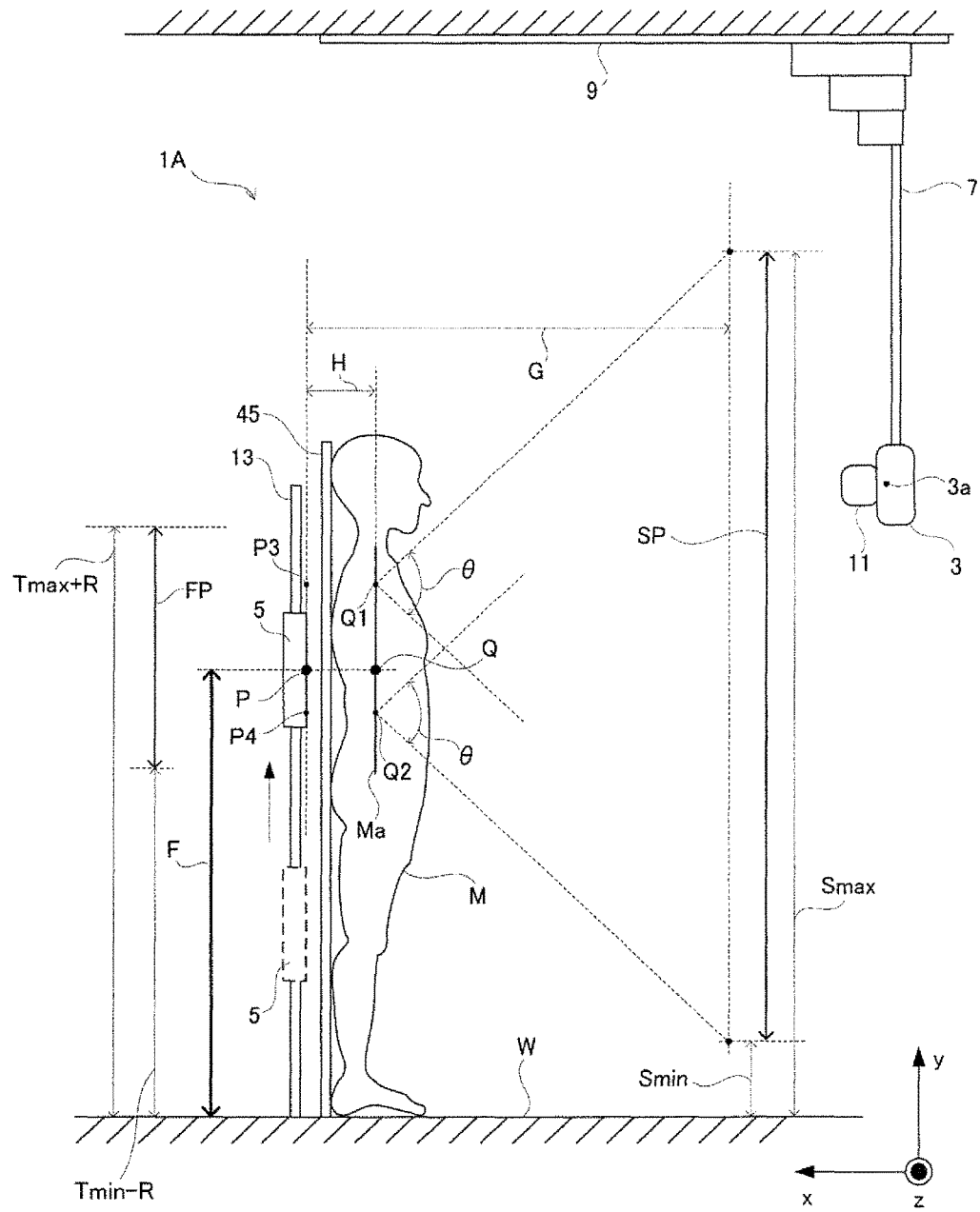
FIG. 13 is a schematic view illustrating the step S2 relative to a radiation tomography imaging device according to the aspect of the Embodiment 2.

Following the calculation of the possible imaging range of the FPD 5 by the imaging range calculation element 35, the position of the FPD 5 is moved. And, first of all, the operator goes to the FPD 5 side to turn off therefor by operating the brake 21. And referring to FIG. 13, the operator manually moves the FPD 5 from the position indicated by the broken line to the position indicated by the solid line corresponding to the position of the target region of the subject M.

When the position of the FPD 5 is out of the possible imaging range FP, i.e., the center point P is not positioned on the straight line P3P4, the alarm sound output element 43 outputs alarm sounds. The operator can make sure the position of the FPD 5 is out of the possible imaging range FP according to the alarm sounds output from the alarm sound output element 43. Once the operator could make sure the position of the FPD 5 is in the range of the possible imaging range FP, the operator turns the brake 21 on to fix the position of the FPD 5.

And the position of the tomography center Q is determined based on the position of the center point P of the detection face of the FPD 5 following fixing the position of the FPD 5. Specifically, the detection element 41 calculates the positional data of the FPD 5 as needed and calculates the height F from the floor surface W to the center point P based on the positional data of the FPD 5. And the detection element 41 calculates the position, having the height F from the floor surface W and the distance F from the center point P in the x-direction, as a tomography center Q. Specifically, the height T from the floor surface W to the tomography center Q is equal to the height F from the floor surface W to the center point P. The memory element 37 stores the positional data of the calculated tomography center Q.

Step S3 (Preparation of an X-Ray Tomography Imaging)

After moving the position of the FPD 5, next a preparation of the X-ray tomography imaging is conducted. Specifically, the operator inputs an instruction to prepare the X-ray tomography imaging by operating the input element 33. According to the instruction input into the input element 33, control signals are output from the main control element 31 to the X-ray tube moving mechanism 15, the X-ray rotation mechanism 19, the supporting element moving mechanism 20 and the FPD moving mechanism 23.

Figure 14:
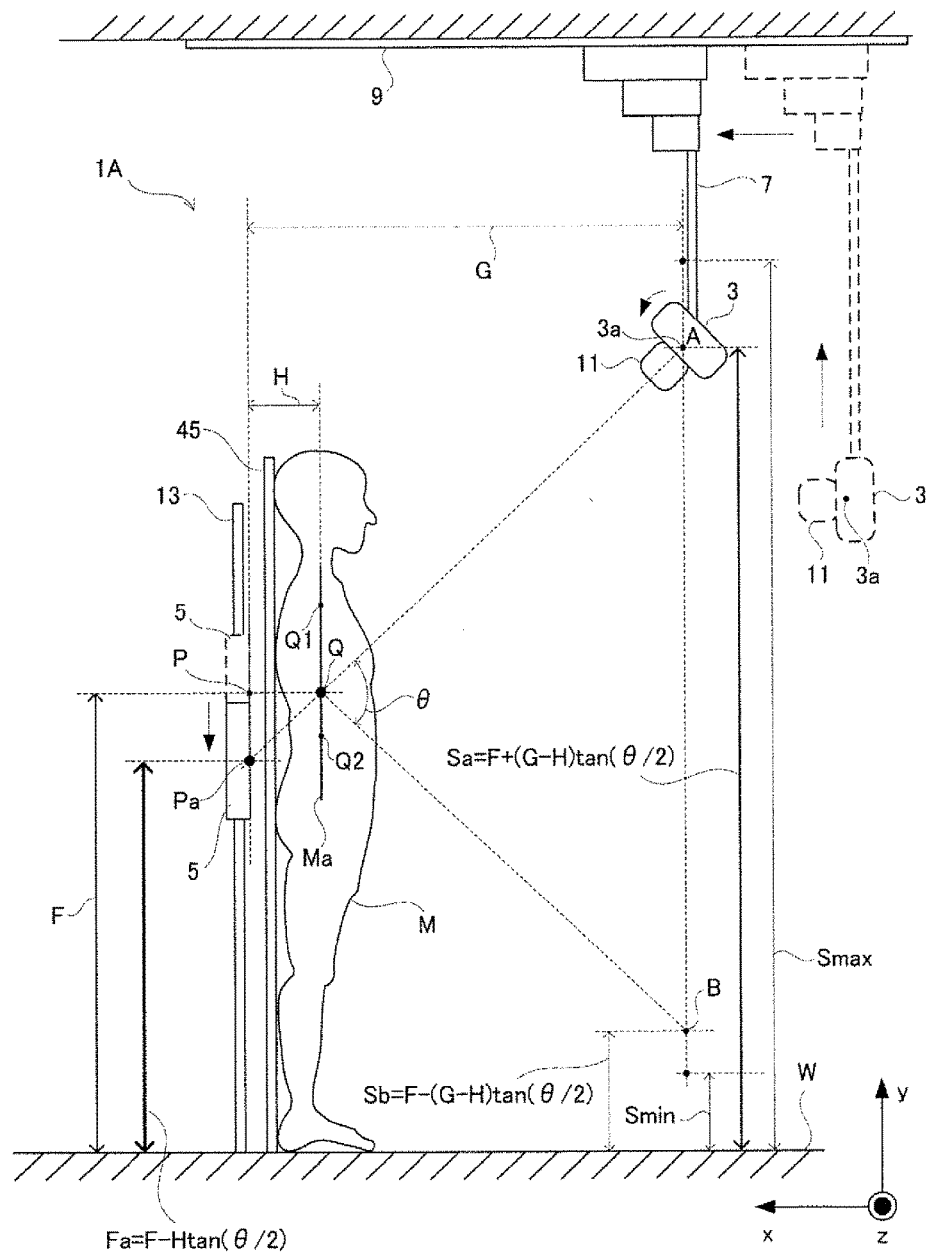
FIG. 14 is a schematic view illustrating the step S3 relative to a radiation tomography imaging device according to the aspect of the Embodiment 2.

The supporting element moving mechanism 20 moves the X-ray tube supporting element 7 in the x-direction based on the given control signals. The X-ray tube moving mechanism 15 moves the X-ray tube 3 in the x-direction based on the given control signals. The X-ray tube rotation mechanism 19 tilts the X-ray tube 3 relative to the y-direction based on the given control signals. As results, referring to FIG. 14, the X-ray tube 3 moves from the position indicated by the broken line to an imaging preparation position indicated by the solid line.

Further, according to the aspect of the Embodiment 2, the imaging preparation position of the X-ray tube 3 coincides with the irradiation start position A of the X-ray tube 3. Specifically, the height from the floor surface W to the X-ray focus point 3a is equal to Sa at the imaging preparation position of the X-ray tube 3. Therefore, as described above, if the height T from the floor surface W to the tomography center Q, the imaging distance G and the irradiation swing angle θ are applied, the height from the floor surface W to the X-ray focus point 3a is (T+(G−H) tan (θ/2).

And, the height T from the floor surface W to the tomography center Q is equal to the height F from the floor surface W to the center point P. Accordingly, the height from the floor surface W to the X-ray focus point 3a is (F+(G−H) tan (θ/2)) at the imaging preparation position of the X-ray tube 3. Further, the length of the imaging distance is G, so that the length of the norm from the X-ray focus point 3a to the detection face of the FPD 5 is G. Accordingly, the imaging preparation position of the X-ray tube 3 is determined based on the height F from the floor surface W to the center point P, the imaging distance G, the irradiation swing angle θ and the tomographic section height H.

Further, the FPD moving mechanism 23 moves the FPD 5 to the detection preparation position based on the received signals in synchronism with moving of the X-ray tube 3 in the y-direction. Further, according to the aspect of the Embodiment 2, the detection preparation position of the FPD 5 coincides with the detention start position Pa of the FPD 5. Therefore, the height from the floor surface W to the center point P is equal to the height Fa from the floor surface W to the detection start position Pa at the detection preparation position of the FPD 5. And as described above, the height Fa from the floor surface W to the detection start position Pa is T−H tan (θ/2).

Specifically, the height T from the floor surface W to the tomography center Q is equal to the height F of the center point P of the FPD 5 moved in the step S2. Therefore, the height from the floor surface W to the center point P is F−H tan (θ/2) at the detection preparation position of the FPD 5. Accordingly, the detection preparation position of the FPD 5 is determined based on the height F of the center point P of the FPD 5 moved in the step S2, the irradiation swing angle θ and the tomographic section height H. The preparation of the X-ray tomography imaging is completed when moving of the X-ray tube 3 to the imaging preparation position and moving of the FPD 5 to the detection preparation position are completed.

Step S4 (Generation of an X-Ray Image)

Figure 15:
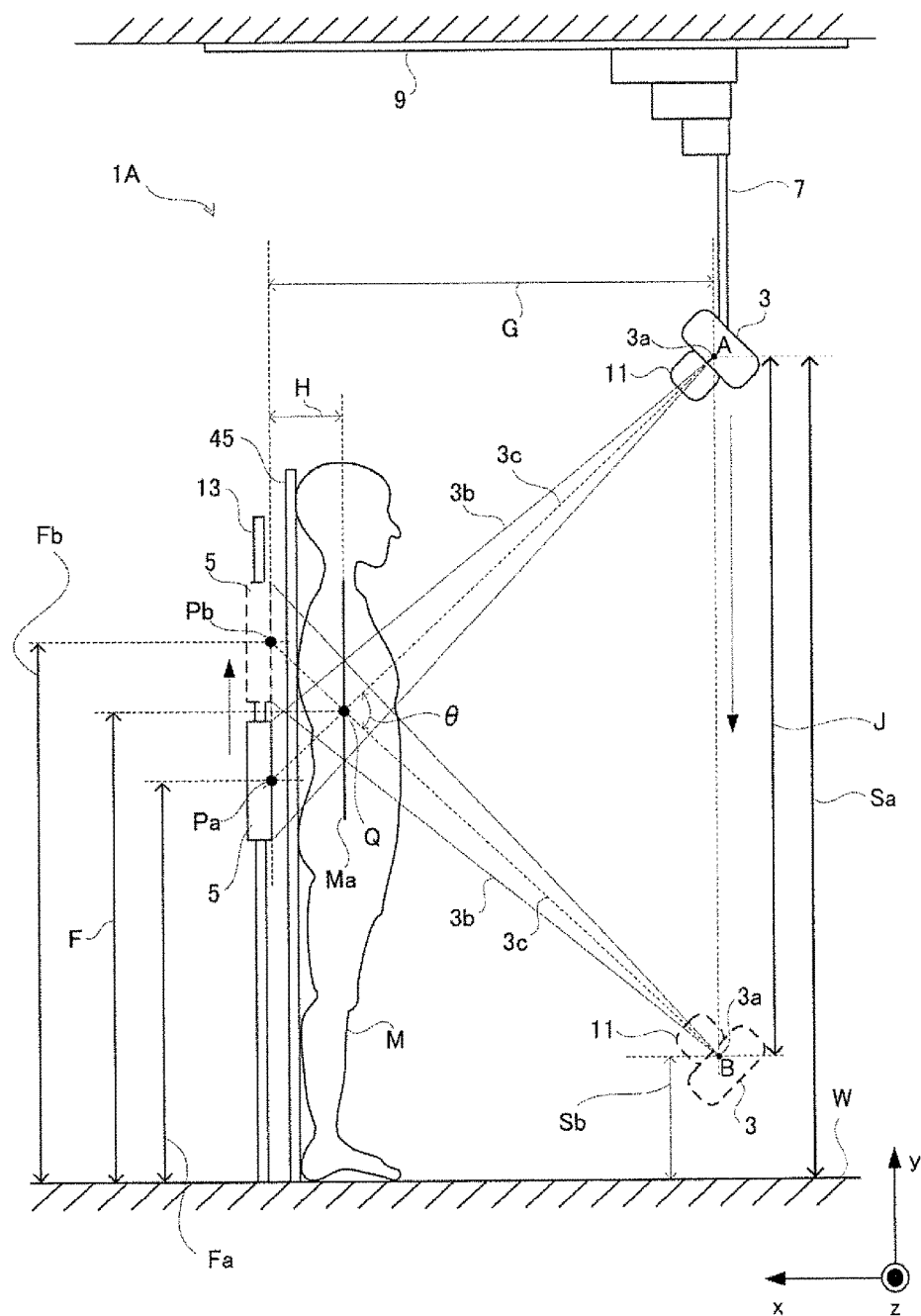
FIG. 15 is a schematic view illustrating the step S4 relative to a radiation tomography imaging device according to the aspect of the Embodiment 2.

Following the completion of the preparation of the X-ray tomography imaging, next an X-ray image is being generated. Specifically, the operator inputs an instruction to start the X-ray irradiation by operating the input element 33. Referring to FIG. 15, the X-ray tube 3 is controlled so as to travel in the straight line from the irradiation start position indicated by the solid line to the irradiation end position indicated by the broken line by the X-ray tube moving mechanism. The FPD 5 is controlled so as to travel in the straight line from the irradiation start position indicated by the solid line to the irradiation end position indicated by the broken line by the FPD moving mechanism 23.

The X-ray irradiation control element 17 irradiates the corn shaped X-ray 3b from the X-ray focus point 3a traveling in the straight line in the y-direction based on the output signals from the main control element 31. The X-ray 3b irradiated transmits the subject M and is being detected by the FPD 5. When detects the X-ray 3b, the FPD 5 outputs the X-ray detection signals and the output X-ray detection signals are sent to the image generation element 25. The image generation element 25 generates X-ray images based on the received X-ray detection signals. The data of the generated X-ray images are sent to the tomography image reconstruction element 27 from the image generation element 25.

At this time, the X-ray rotation mechanism 19 tilts the X-ray tube 3 relative to the y-direction so that the center axis 3c of the X-ray 3b can pass always the target region Q in synchronism with moving of the X-ray tube 3 in the y-direction. Specifically, the X-ray rotation mechanism 19 rotates the X-ray tube 3 around the axis of the z-direction and controls the tilt angle of the X-ray tube 3 relative to y-direction based on the signals received from the main control element 31.

Step S5 (Acquisition of an X-Ray Tomography Image)

Once a series of X-ray images is generated, the tomography image reconstruction element 27 reconstructs the data relative to the series of X-ray images. According to the reconstruction of image data relative to the X-ray image, an X-ray tomography image data of the subject M at the desired cross section position can be acquired. The monitor 29 displays the X-ray tomography images acquired by the tomography image reconstruction element 27.

(Effects of a Configuration According to the Aspect of the Embodiment 2)

In such way, the imaging range calculation element 35 calculates the possible imaging range of the FPD 5 prior to imaging of the X-ray tomography imaging in the radiation tomography imaging device 1A according to the aspect of the Embodiment. First, the operator calculates a possible imaging range of the X-ray tube 3 based on the imaging distance G, the irradiation swing angle θ, the tomographic section height H and the possible imaging range SP of the X-ray tube 3. The imaging distance G, the irradiation swing angle θ and the cross section height H are parameters that the operator determines preliminarily and arbitrarily every time when the X-ray tomography images are imaged. And the movable range SP of the X-ray tube 3 is a predetermined parameter relative to the radiation tomography imaging device 1. Accordingly, the operator can calculates preliminarily a possible imaging range of the FPD 5 prior to moving start of the X-ray tube based on such parameters.

The possible imaging range of the FPD 5 can be calculated prior to moving start of the X-ray tubes, so that the operator moves the FPD 5 into the possible imaging range without fail and then can start moving the X-ray tube. The possible imaging range of the FPD 5 is the positional range of the FPD 5 in which the X-ray tomography images can be imaged without moving the moving region of the X-ray tube 3 to the outside of movable range of the X-ray tube 3. Therefore, during the X-ray tomography imaging, an incident in which the X-ray tube is interfered by the floor surface and so forth, or an incident in which the X-ray tomography imaging is suspended in the middle thereof by sensing any possible interference with the X-ray tube 3 can be avoided, so that the X-ray tomography imaging can be performed adequately and efficiently.

And the X-ray tube and the FPD 5 move synchronously in the opposite direction each other in the radiation tomography imaging device 1A according to the aspect of the Embodiment 2, so that X-ray tomography images over broader region can be acquired. Specifically, when the X-ray tomography imaging is conducted while fixing the position of the FPD 5, the region U where all X-ray images so as to reconstruct X-ray tomography images can be generated is indicated by diagonal lines referring to FIG. 16(a). In such case, the region U of the anterior side of the subject M becomes particularly narrow. Specifically, if the target region is in the anterior side of the subject M, the acquisition of the X-ray tomography image may become difficult.

On the other hand, according to the aspect of the Embodiment 2, when the X-ray tube 3 and the FD 5 move synchronously each other in the opposite direction, the region U is indicated by the orthogonal lines referring to FIG. 16B. Accordingly, even when the target region is in the anterior side of the subject M, the X-ray tomography image can be obtained adequately. Accordingly, in the radiation tomography imaging device 1A according to the aspect of the Embodiment 2, the X-ray tomography imaging of the broader target region can be performed adequately and efficiently compared to the system in which the position of the FPD is fixed.

Embodiment 3

Next, referring to FIGS., the inventors set forth the Embodiment 3 of the present invention. Further, the configuration and steps of an operation according to the aspect of the Embodiment 3 are the same as the radiation tomography imaging device 1 according to the aspect of the Embodiment 1 or the radiation tomography imaging device 1A according to the aspect of the Embodiment 2, so that the inventor skips the detail description.

Figure 17A:
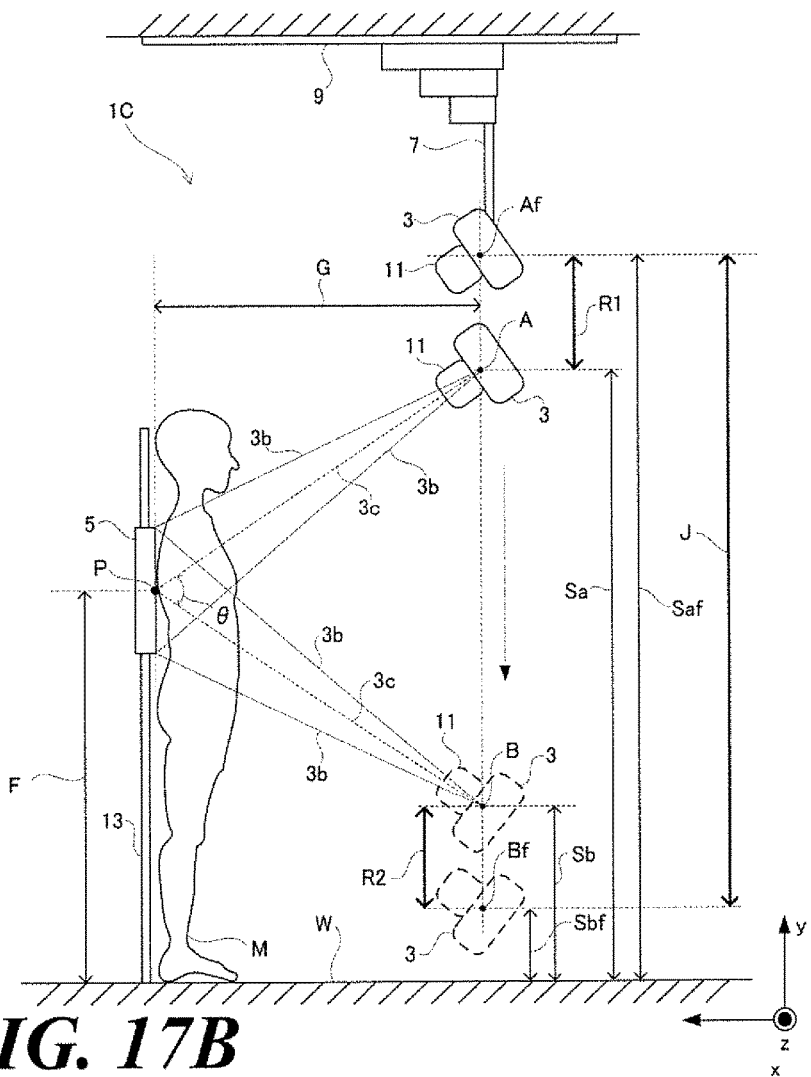
FIG. 17A, 17B are schematic views illustrating a structure of a radiation tomography imaging device according to the aspect of the Embodiment 3.

However, according to the aspects of the Embodiment 1 and Embodiment 2, the imaging preparation position of the X-ray tube 3 coincides with the irradiation start position A of the X-ray tube 3. On the other hand, according to the aspect of the Embodiment 3 referring to FIG. 17A, the imaging preparation position of the X-ray tube 3 indicated by the sign Af is different from the position of the irradiation start position A of the X-ray tube 3. In such way, the Embodiment 3 is different from the Embodiment 1 and the Embodiment 2 with regard to the points relative to whether the imaging preparation position of the X-ray tube 3 coincides with the position of the irradiation start position of the X-ray tube 3 or not. Further, hereafter, a distance from the imaging preparation position Af to the irradiation start position A is an acceleration distance R1 and a distance from the imaging end position Bf to the irradiation end position B is a deceleration distance R2.

According to the aspect of the Embodiment 3, the X-ray tube that has moved to the imaging preparation position Af in the step S3 starts moving in the y-direction along the X-ray tube supporting element 7 following initiation of the step S4 (FIG. 17A, 17B), t0.) And the X-ray tube 3 starts irradiation of the X-ray 3b to the subject M at the position of the irradiation start position A. Then after, the X-ray tube 3 moves from the irradiation start position A to the irradiation end position B at the constant velocity while intermittently irradiating the X-ray 3b. The X-ray tube 3 ends the X-ray 3b irradiation at the position of the irradiation end position B (t2.). Then the X-ray tube 3 moves from the irradiation end position B to the imaging end position Bf while decelerating and suspends the moving at the imaging end position Bf (t3.)

Figure 17B:
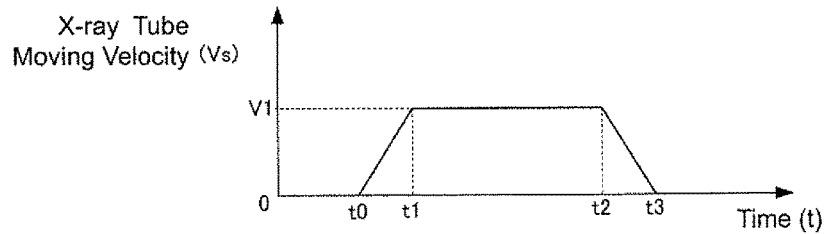

The moving velocity Vs of the X-ray tube 3 is illustrated in the FIG. 17B during such operation. The moving velocity Vs accelerates from the start time t0 until the time t1 and reaches a constant velocity V1 at the time t1. The moving velocity Vs maintains a constant velocity V1 from the time when the X-ray tube 3 reaches to the irradiation start position A at the time t1 until the time when the X-ray tube 3 reaches to the irradiation end position B at the time T2. Then after, the moving velocity Vs decelerates from the time t2 until the time t3. Then the moving velocity Vs becomes 0 at the time t3 when the X-ray tube 3 reaches to the imaging end position Bf and the X-ray tube 3 suspends moving thereof.

(According to the Aspect of the Embodiment 3, a Calculation Method of the Possible Imaging Range of the FPD)

Relative to the radiation tomography imaging device 1C according to the aspect of the Embodiment 1, the inventor sets forth the method how the imaging range calculation element 35 can calculate the possible imaging range of the FPD 5. Further, the height from the floor surface W to the imaging preparation position Af is Saf and the height from the floor surface W to the imaging end position Bf is Sbf.

Figure 18:
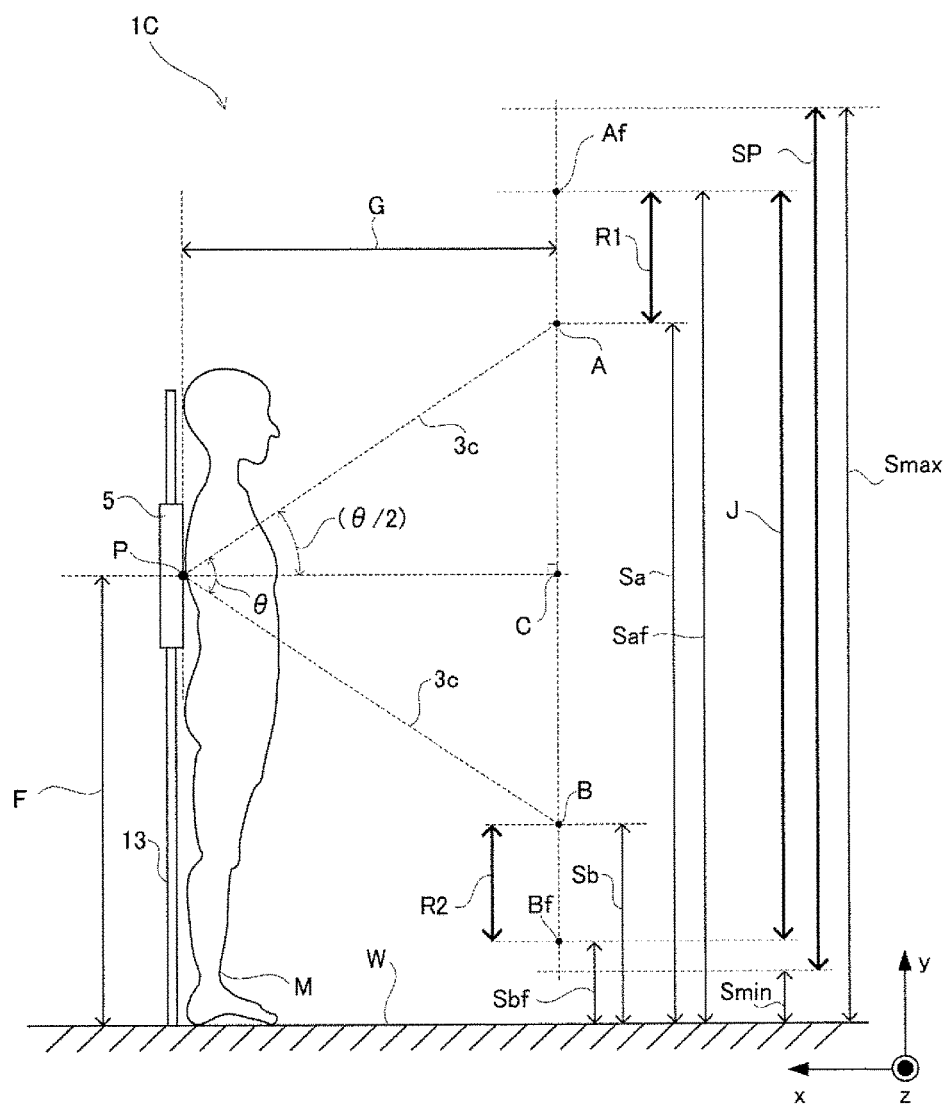
FIG. 18 is illustrating a calculation method for a height of the X-ray focus point based on a height of a target region, an imaging distance, and an irradiation swing angle relative to a radiation tomography imaging device according to the aspect of the Embodiment 3.

Referring to FIG. 18, when the position of the FPD 5 is fixed while an X-ray tomography imaging, the height Saf and the height Sbf can be calculated by using the height F from the floor surface W to the center point P of the detection face of the FPD 5, the imaging distance G and the irradiation swing angle θ. Here, if an intersection of the normal line of the detection face of the FPD 5 passing the center point P and the straight line AB is C, either degree of ∠APC or ∠BPC is θ/2. Specifically, either length $D_{AC}$ of the straight line AC or the length $D_{BC}$ of the straight line $D_{BC}$ is G tan (θ/2), so that the height Saf and the height Sbf can be calculated using the following formulae (12) and (13).

$$Saf = F + D_{AC} + R1 = F + G \tan(\theta/2) + R1 \quad (12)$$

$$Sbf = F - D_{BC} - R2 = F - G \tan(\theta/2) - R2 \quad (13)$$

The moving region J of the X-ray tube 3 must be always within the range of the movable range SP of the X-ray tube 3. Therefore, the maximum $S_{max}$ of the height S from the floor surface W to the X-ray focus point 3a is always longer than the height Saf, and the minimum $S_{min}$ of the height S is always shorter than the height Sbf, so that $S_{max} \geq Saf$ and $S_{min} \leq Sbf$ can be completed. Accordingly, the range of the height F from the floor surface W to the center point P of detection face of the FPD 5 can be calculated using the below formula (14).

$$S_{max} - G \tan(\theta/2) \geq F \geq S_{min} + G \tan(\theta/2) \quad (14)$$

Here, the maximum of the height F calculated by the above formula (14), i.e., $S_{max} - G \tan(\theta/2) - R1$ is specified as $F_{max}$. And, the minimum of the height F calculated by the above formula (4), i.e., $S_{min} + G \tan(\theta/2) + R2$ is specified as $F_{min}$. Further, the length from the center point P of the FPD 5 to the upper end of the FPD 5 and the length from the center point P of the FPD 5 to the lower end of the FPD 5 are R. In such case, the possible imaging range FP of the FPD 5 is specified as the range between the upper limit ($F_{max}$+R) and the lower limit ($F_{min}$-R) by using $F_{max}$, $F_{min}$ and R.

Accordingly, the imaging range calculation element 35 can calculate the movable range FP of the FPD 5 by using a parameter such as the imaging distance G and so forth. The imaging distance G and the irradiation swing angle θ among the parameters applied to the calculation of the possible imaging range FP are the parameters preliminarily determined arbitrarily by the operator every time when an X-ray tomography imaging is conducted. And $S_{max}$ and $S_{min}$ are predetermined parameters in accordance with a specification of the X-ray tube 3 and a size of an examination room. In addition, the length of R is predetermined value based on the size of the FPD 5.

And, an acceleration velocity R1 and a deceleration velocity R2 are determined based on the weight of the X-ray tube 3 and the moving velocity V1 of the X-ray tube 3 when irradiating an X-ray. Specifically, the acceleration velocity R1 and the deceleration velocity R2 are predetermined parameters in accordance with a specification of the radiation tomography imaging device 1. Accordingly, according to the aspect of the Embodiment 3 referring to FIG. 18, the operator can preliminarily calculate the possible imaging range FP of the FPD 5 prior to the radiation tomography imaging using the predetermined parameters.

Figure 19:
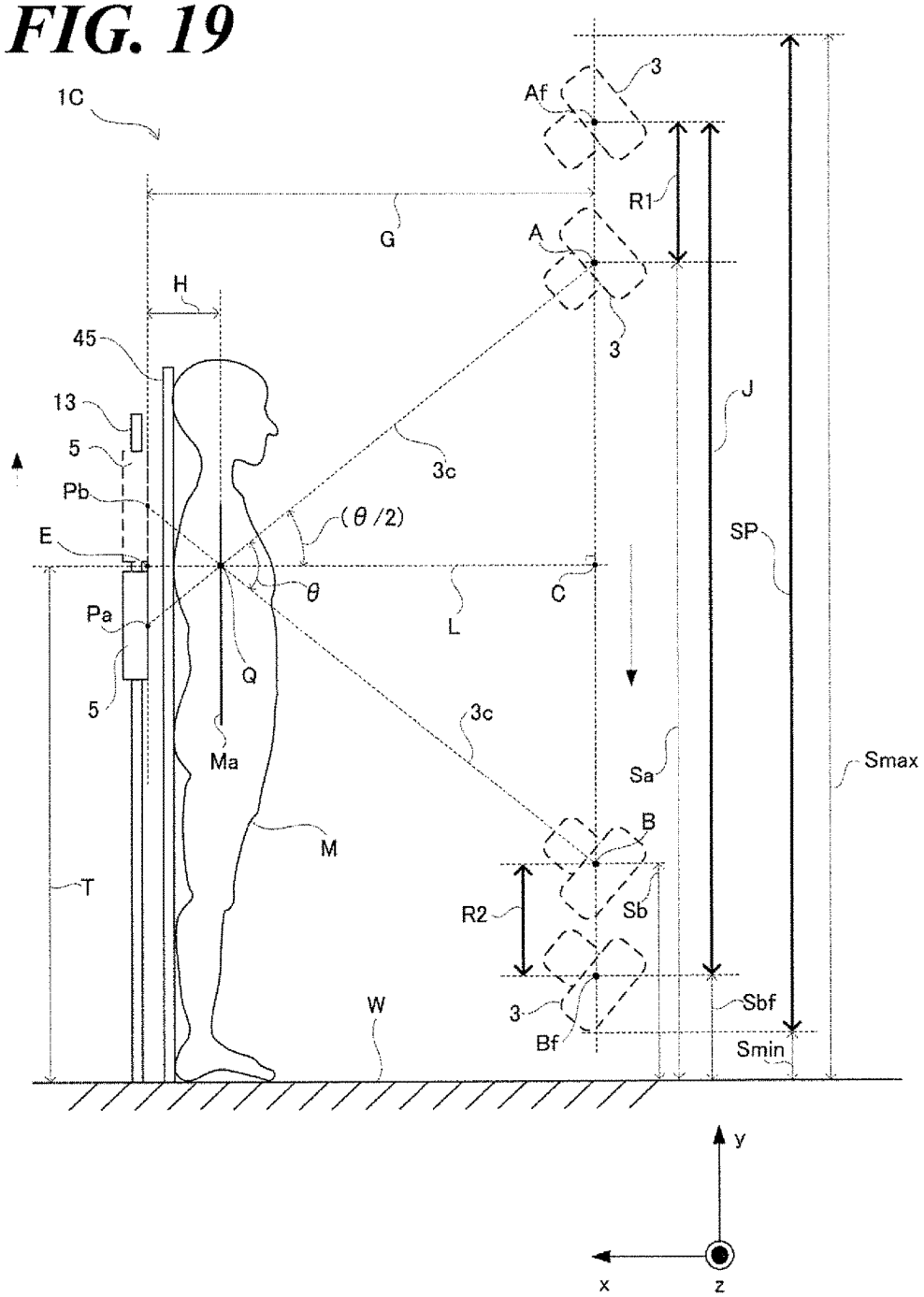
FIG. 19 is illustrating a calculation method for a height of an X-ray focus point based on a height of a target region, an imaging distance, an irradiation swing angle and a cross section height.
Figure 20A:
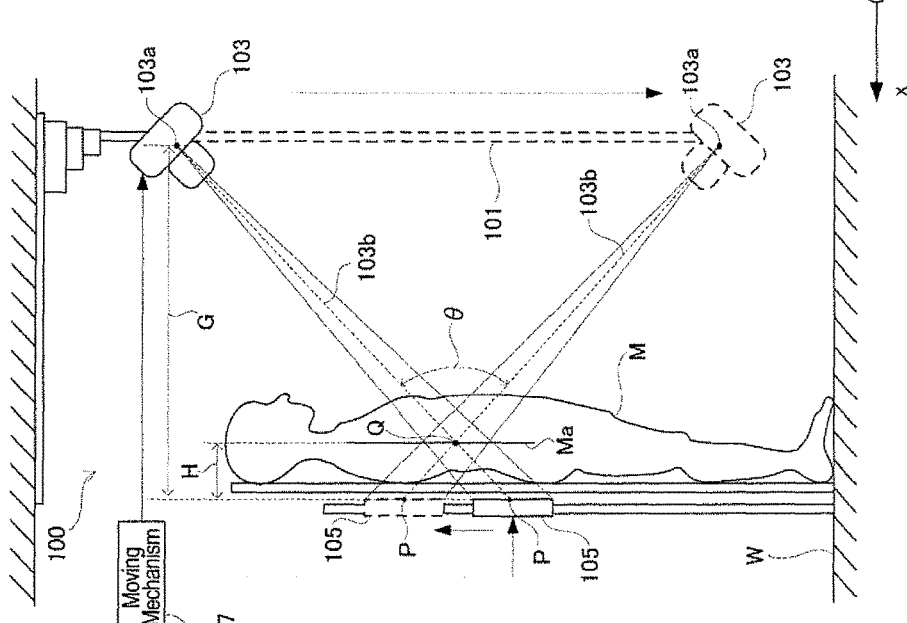
FIG. 20A, 20B are schematic views illustrating a structure of an X-ray tomography imaging apparatus according to the aspect of the conventional example.
Figure 20B:
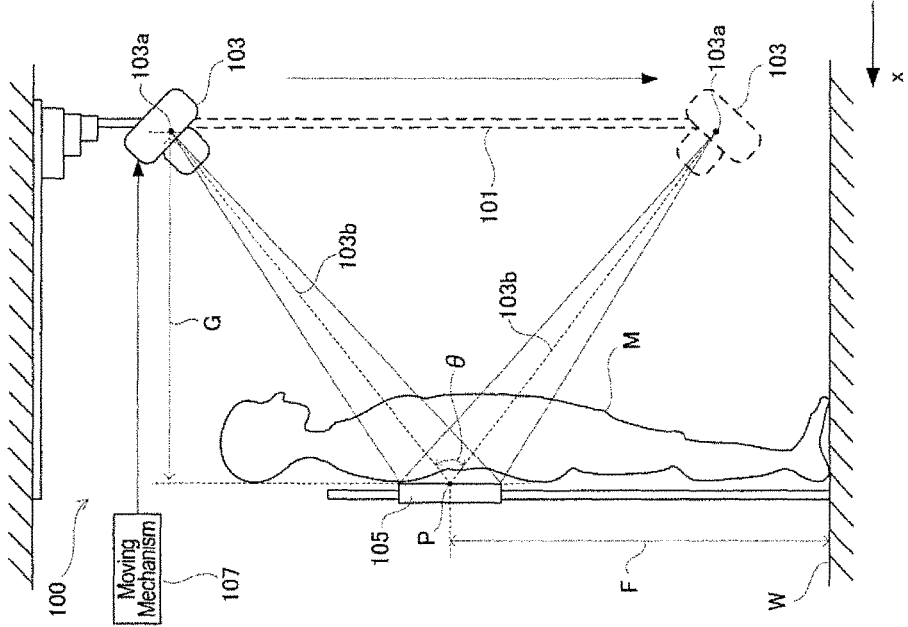
Figure 21:
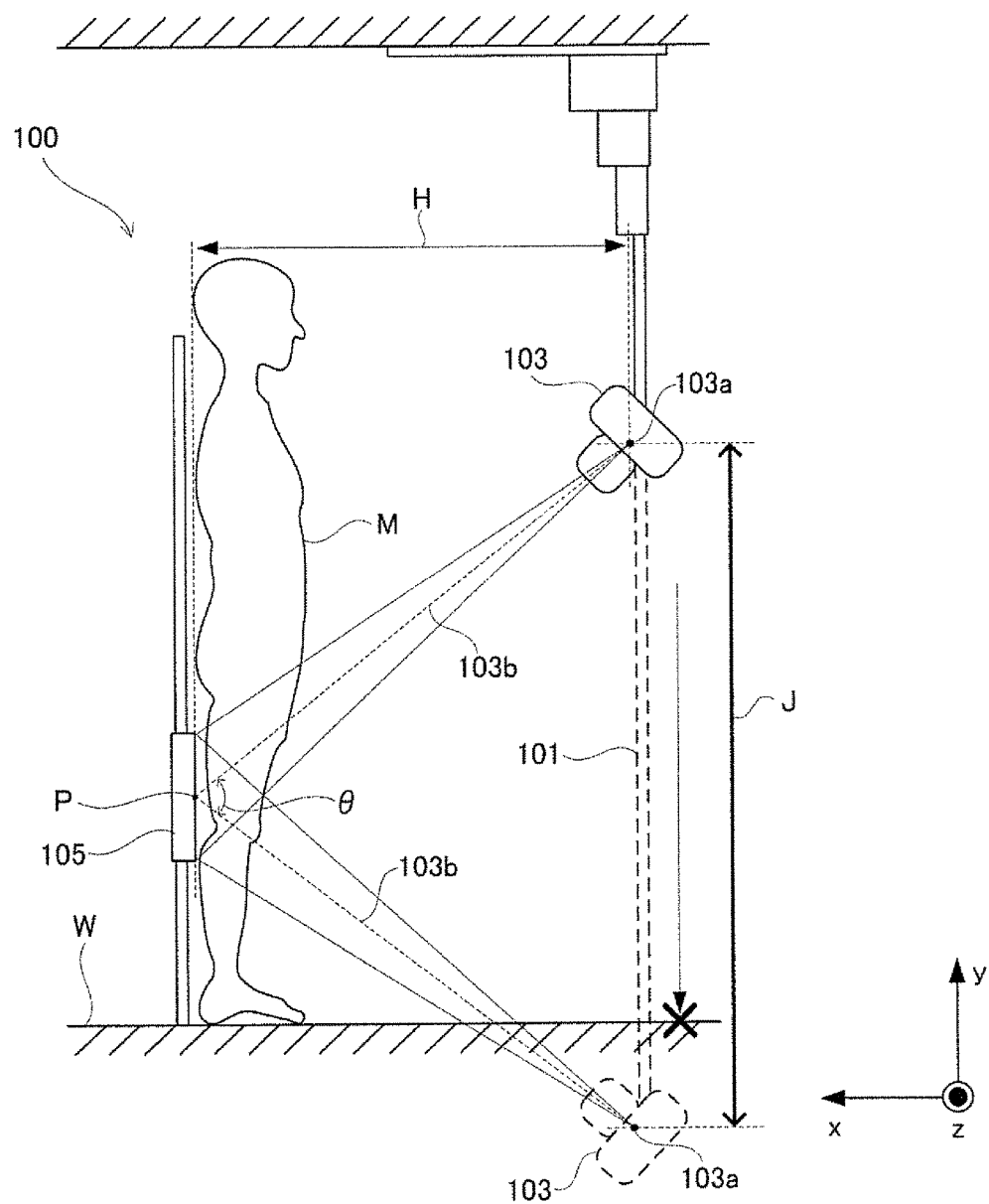
FIG. 21 is a schematic view illustrating a problematic structure of a radiation tomography imaging device according to the aspect of the conventional example.
Figure 22A:
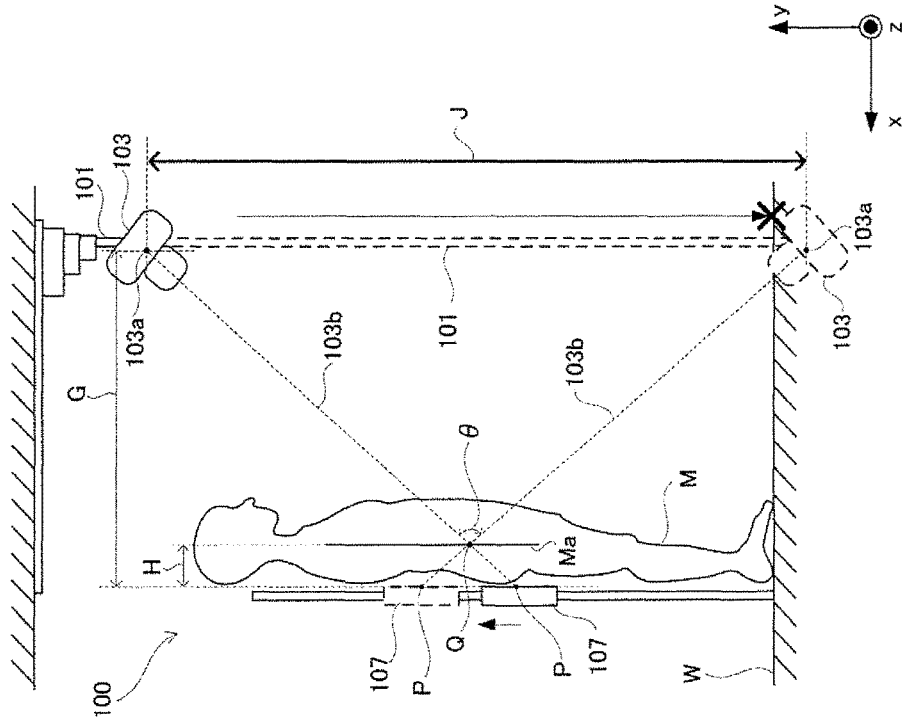
FIG. 22A, 22B are schematic views illustrating a problematic structure of a radiation tomography imaging device according to the aspect of the conventional example.
Figure 22B:
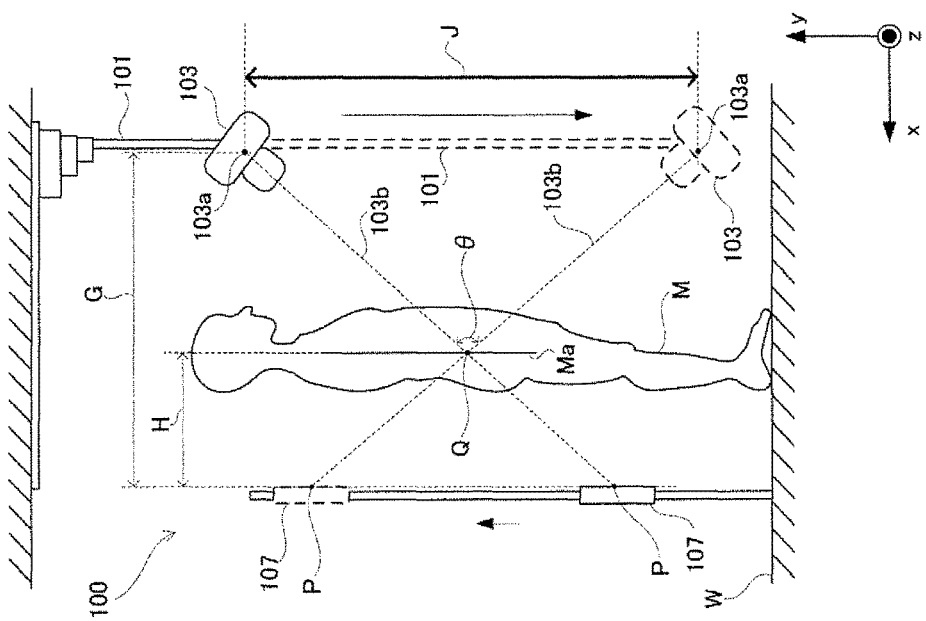

In addition, referring to FIG. 19, according to the aspect of the Embodiment 3, when the FPD is structured to move facing the X-ray tube 3 while an X-ray tomography imaging, the height Saf and the height Sbf can be calculated as follows using the height T from the floor surface W to the target region Q, the imaging distance G, the swing angle θ and the tomographic section height H.

The intersection of the normal L downed from the target region Q to the detection face of the FPD 5 and the straight line AB is C and the intersection of the normal L and the straight line PaPb is E. In such case, either degree of ∠AQC or ∠BQC is (θ/2.) Further, the length of the straight line CQ is (G−H), the length $D_{AC}$ of the straight line AE and the length $D_{BC}$ of the straight line BC are (G−H) tan (θ/2). Specifically, the height Saf and the height Sbf can be calculated using the following formulae (15) and (16).

$$Saf = T + D_{AC} + R1 = T + (G-H)\tan(\theta/2) + R1 \quad (15)$$

$$Sbf = T - D_{BC} - R2 = T - (G-H)\tan(\theta/2) - R2 \quad (16)$$

The moving region J of the X-ray tube 3 must be always within the range of the movable range SP, so that formulae $S_{max} \geq SA$ and $S_{min} \leq SB$ can be completed. Accordingly, the range of the height T from the floor surface W to the target region Q can be calculated using the below formulae (17) and (18).

$$S_{max} - (G-H)\tan(\theta/2) - R1 \geq T \quad (17)$$

$$S_{min} + (G-H)\tan(\theta/2) + R2 \leq T \quad (18)$$

Here, the maximum of the height F calculated by the above formula (17), i.e., $S_{max} - (G-H) \tan(\theta/2) - R1$ is specified as $T_{max}$. And, the minimum of the height F calculated by the above formula (18), i.e., $S_{min}$+(G–H) tan (θ/2)+R2 is specified as $T_{min}$. In addition, the length from the center point P of the FPD 5 to the upper end of the FPD 5 and the length from the center point P of the FPD 5 to the lower end of the FPD 5 is R. In such case, the possible imaging range FP of the FPD 5 is specified as the range between the upper limit ($F_{max}$+R) and the lower limit ($F_{min}$–R) by using $F_{max}$, $F_{min}$ and R as well as the aspect of the Embodiment 2.

(Effects of a Configuration According to the Embodiment 3)

Accordingly, the imaging range calculation element 35 can calculate the movable range FP of the FPD 5 by using a parameter such as the imaging distance G and so forth. Any parameter applied to calculate the possible imaging range FP is the parameter that can be predetermined prior to imaging the X-ray tomography imaging. Accordingly, according to the aspect of the Embodiment 3 referring to FIG. 19, the operator can also preliminarily calculate the possible imaging range FP of the FPD 5 prior to the X-ray tomography imaging using the group consisting of predetermined parameters.

The operator can preliminarily calculate the possible imaging range FP of the FPD 5 prior to imaging the X-ray tomography imaging, so that the operator can start imaging the X-ray tomography imaging under the situation in which the FPD 5 is certainly within the range of the possible imaging range FP of the FPD 5. As results, relative to the radiation tomography imaging device 1C according to the aspect of the Embodiment 3, the moving of the X-ray tube 3 out of the movable range SP can be avoided when the X-ray tomography imaging is conducted so that the imaging of the X-ray tomography imaging can be performed adequately.

Relative to the radiation tomography imaging device 1C according to the aspect of the Embodiment 3, an acceleration distance R1, in which the moving velocity Vs of the X-ray tube 3 is accelerated, is installed between the imaging preparation position Af and the irradiation start position A. In addition, a deceleration distance R2 in which the moving velocity Vs of the X-ray tube 3 is decelerated is installed between the irradiation end position 13 and the imaging end position Bf of the X-ray tube 3.

Specifically, the moving velocity Vs is accelerated while the X-ray tube 3 travels from the imaging preparation position A to the irradiation start position A in the step S4 and reaches to the constant velocity V1 at the irradiation start position A. Then, the X-ray tube 3 travels from the irradiation start position A to the irradiation end position B keeping the velocity V1 while intermittently irradiating the X-ray 3b. Then the moving velocity is decelerated while the X-ray tube 3 is moving from the irradiation end position B to the imaging end position Bf while decelerating and suspends moving at the imaging end position Bf at which the moving velocity Vs becomes 0.

According to such structure, relative to the radiation tomography imaging device 1C according to the aspect of the Embodiment 3, the X-ray tube 3 can intermittently irradiate X-ray while moving in a constant velocity and can generate a series of X-ray images. At this time, the moving velocity of the X-ray tube 3 is constant, so that the timing when the intermittent irradiation of the X-ray to generate the series of X-ray images can be further easily calculated. Therefore, a control to image the adequate X-ray tomography images can be more accurately and more easily conducted.

The present invention is not limited to the aspect of the Embodiments set forth above and furthers another alternative Embodiment can be implemented set forth below.

(1) According to the aspect of above described each Embodiment, the X-ray tube rotation mechanism 19 tilts the X-ray tube 3 relative to the y-direction so that the center axis 3c of the X-ray 3b can pass always the center point P of the detection face of the FPD 5, but such structure is not limited thereto. Specifically, a point (center point of an X-ray irradiation region) through which the center axis 3c of the X-ray 3b always passes can be any point of the detection face of the FPD 5. In such alternative Embodiment, the center point P of the FPD 5 is replaced by the position of the center point of the X-ray irradiation region on the detection face of the FPD 5 as needed and then a possible imaging range FP of the FPD 5 can be calculated.

A size of the FPD 5 and a size of the X-ray irradiation region may be different depending on the conditions for the X-ray imaging. In such case, the position of the X-ray irradiation region may be out of the center of the detection face of the FPD 5. Relative to the radiation tomography imaging device according to the aspect of the alternative Embodiment, the possible imaging range FP of the FPD 5 can be accurately calculated even when the position of the X-ray irradiation region may be out of the center of the detection face of the FPD 5.

(2) According to the aspect of above described each Embodiment, the possible imaging range FP is calculated as the length from the center point P of the FPD 5 to the upper end of the FPD 5 and the length from the center point P of the FPD 5 to the lower end of the FPD 5 are R, but not limited thereto. Specifically, the length R may be replaced by the length from the center point P (or the center point of the X-ray irradiation region) to the upper end of the X-ray irradiation region (or the lower end) to calculate the possible imaging range FP of the FPD 5.

(3) According to the aspect of above described each Embodiment, when FPD 5 is out of the possible imaging range FP, the FPD moving mechanism 23 can be configured to be controlled so that the FPD 5 can travel in the range of the possible imaging range FP. Specifically, when the FPD 5 is out of the possible imaging range FP, the main control element 31 sends a signal to the moving mechanism 23. The FPD moving mechanism 23 turns the brake 21 off to move the FPD in the y-direction based on the control signal.

And, when the FPD 5 has moved into the possible imaging range FP, the FPD detection element 41 calculates the position of the FPD 5 and sends a signal to the moving mechanism 23 via the main control element 31 The FPD moving mechanism 23 turns the brake 21 on to suspend moving of the FPD 5 based on the control signal. According to such structure, the position of the FPD 5 is absolutely in the possible imaging range FP. Therefore, during the X-ray tomography imaging, an incident in which the X-ray tube 3 is interfered by the floor surface and so forth, or an incident in which the X-ray tomography imaging is suspended in the middle thereof by sensing any possible interference with the X-ray tube 3 can be absolutely avoided.

In addition, when the position of the FPD 5 changes from the possible imaging range FP to the outside of the possible imaging range FP, the structure, in which the FPD moving mechanism 23 turns the brake 21 on, can be adopted. Specifically, the FPD detection element 41 calculates the position of the FPD 5, and when the position of the FPD 5 changes to outside of the possible imaging range FP, the main control element 31 send a signal to the moving mechanism 23. The FPD moving mechanism 23 turns the brake 21 on to suspend moving of the FPD 5 based on the control signal.

According to such structure, it is absolutely avoidable that the position of the FPD 5 shifts to the outside of the possible imaging range FP of the FPD 5. Therefore, when the operator tries erroneously to move manually the FPD 5 to the outside of the possible imaging range FP or after the moving of the FPD 5 is completed in the step S2, and then even if the operator forgets to set the brake on, an incident in which the position of the FPD 5 is out of the possible imaging range FP can be avoided. Therefore, during the X-ray tomography imaging, an incident in which the X-ray tube is interfered by the floor surface and so forth, or an incident in which the X-ray tomography imaging is suspended in the middle thereof by sensing any possible interference with the X-ray tube 3 can be absolutely avoided.

(4) According to the aspect of above described each Embodiment, when the FPD 5 is out of the possible imaging range FP, it is structured that the alarm sound output element 43 outputs alarm sounds, but a means to notify that the FPD 5 is out of the possible imaging range FP is not limited to the alarm sounds. Specifically, it is structured that e.g., LED lamp or other display elements may blink or light. In addition, a warning message is displayed, so that the incident in which the FPD 5 is out of the possible imaging range FP can be notified.

(5) According to the aspect of above described each Embodiment, a base of the X-ray tube supporting element 7 is installed on the ceiling of the examination room and moves horizontally along with a rail 9 installed in the x-direction, but not limited thereto. Specifically, a base of the X-ray tube supporting element 7 may have the base thereof on the floor surface W and may move horizontally along with a rail 9 installed in the x-direction.

(6) According to the aspect of above described each Embodiment, it is structured that the irradiation start position A is in place in the upper stream of the irradiation end position B and the X-ray tube 3 moves from the upper side to the lower side, but not limited thereto. Specifically, the irradiation start position A is in place in the lower side of the irradiation end position B and the X-ray irradiation may be intermittently conducted while moving from the lower side to the upper side, (7) According to the aspect of above described each Embodiment, it is structured that the X-ray tomography image is conducted relative to the subject M in the standing posture, but each Embodiment can be applied to a subject in a lie position.

REFERENCE OF SIGN

1 Radiation tomography device
3 X-ray tube (Radiation source)
5 FPD (Detection means)
7 X-ray tube support element
11 Collimator
15 X-ray tube moving mechanism (Radiation source moving mechanism)
17 X-ray irradiation control element (Radiation source control means)
19 X-ray tube rotation mechanism
23 FPD moving mechanism (Detector moving means)
25 image generation element (Image generation means)
27 Tomography image reconstruction element (Tomography acquisition means)
29 Monitor
31 Main control element (Detector moving control means)
33 Input element
35 Possible imaging range calculation element (Possible imaging range calculation means)
37 Memory element
39 X-ray tube detection element
41 FPD detection element (Detector position calculation means)
43 Alarm sound output element (Alarm means)

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A radiation tomography imaging device, comprising:
a radiation source that irradiates a radiation;
a radiation detector that detects the radiation transmitted through the subject;
a radiation source moving system that moves said radiation source in the body axis direction of a subject;
a radiation irradiation control circuit that controls said radiation source so as to repeatedly irradiate the radiation while said radiation source moving system is moving said radiation source;
an image generation circuit that generates a radiation image using a detection signal output from said radiation detector every radiation irradiation from said radiation source;
a tomography image acquisition circuit that acquires a radiation tomography image by reconstructing a plurality of radiation images generated by the image generation circuit;
a possible imaging range calculation circuit that calculates a possible imaging range of said radiation detector before generating a radiography by said radiation irradiation based on a group consisting of parameters comprising an imaging distance from the focus point of said radiation source to a detection face of said radiation detector, an irradiation swing angle that is the swing angle of said radiation source while said radiation irradiation circuit allows said radiation source to repeatedly irradiate the radiation and a movable range of said radiation source; and
wherein said possible imaging range of said radiation detector is a positional range of said radiation detector where said tomography image acquisition circuit can acquire radiation images without said radiation source departing from a movable range of said radiation source.

2. A radiation tomography imaging device, comprising:
a radiation source that irradiates a radiation;
a radiation detector that detects the radiation transmitted through the subject;
a radiation source moving system that moves said radiation source in a body axis direction of a subject;
a radiation irradiation control circuit that controls said radiation source so as to repeatedly irradiate the radiation while said radiation source moving system is moving said radiation source;

an image generation circuit that generates a radiation image using a detection signal output from said radiation detector every radiation irradiation from said radiation source;

a tomography image acquisition circuit that acquires a radiation tomography image by reconstructing a plurality of radiation images generated by said image generation circuit;

a detector moving system that moves in the opposite direction of the moving direction of said radiation source moved by said radiation source moving system while said radiation detector and said radiation source are facing each other and sandwiching said subject; and a possible imaging range calculation circuit that calculates a possible imaging range of said radiation detector before generating a radiography by said radiation irradiation based on a group consisting of parameters comprising an imaging distance from the focus point of said radiation source to a detection face of said radiation detector, an irradiation swing angle that is the swing angle of said radiation source while said radiation irradiation circuit allows said radiation source to repeatedly irradiate the radiation, a movable range of said radiation source, and a tomographic section height is a distance from the detection face of said radiation detector to the center of the tomography center point; and wherein said possible imaging range of said radiation detector is a positional range of said radiation detector where said tomography image acquisition circuit can acquire radiation images without said radiation source departing from a movable range of said radiation source.

3. The radiation tomography imaging device according to claim 1, wherein:

said group consisting of parameters further includes an acceleration distance that is the distance, while said radiation source moves during being accelerated, from an imaging preparation position of said radiation source to the imaging start position, and a deceleration distance that is the distance while said radiation source moves during being decelerated, from an irradiation ending position of said radiation source to an imaging ending position.

4. The radiation tomography imaging device according to claim 1 comprising:

an input element that inputs said group consisting of said parameters;

wherein said possible imaging range calculation circuit calculates the possible imaging range of said radiation detector based on said group consisting of parameters input in said input element every time when said group consisting of parameters is input into said input element.

5. The radiation tomography imaging device according to claim 1 comprising:

a detector position calculation circuit that calculates a position of said radiation detector.

6. The radiation tomography imaging device according to claim 5 comprising:

an alarm circuit that alarms when a position of said radiation detector calculated by said detector position calculation circuit is out of the possible imaging range of said radiation detector.

7. The radiation tomography imaging device according to claim 5 comprising:

a detector moving control circuit that controls a detector moving system so as to move said radiation detection circuit within the possible imaging range when the position of said radiation detection circuit calculated by said detector position calculation circuit is out of the possible imaging range of said radiation detector.

8. A radiation tomography imaging device, comprising:

a radiation source that irradiates a radiation;

a radiation detector that detects the radiation transmitted through the subject;

a radiation source moving system that moves said radiation source in the body axis direction of a subject, a radiation irradiation control circuit that controls said radiation source so as to repeatedly irradiate the radiation while said radiation source moving system is moving said radiation source;

an image generation circuit that generates a radiation image using a detection signal output from said radiation detector every radiation irradiation from said radiation source;

a tomography image acquisition circuit that acquires a radiation tomography image by reconstructing a plurality of radiation images generated by the image generation circuit, a possible imaging range calculation circuit that calculates a possible imaging range of said radiation detector, which is a positional range of said radiation detector, wherein said radiation source is in the movable range of said radiation source and said detection circuit can acquire said radiation tomography image based on a group consisting of parameters comprising an imaging distance from the focus point of said radiation source to a detection face of said radiation detector, an irradiation swing angle that is the swing angle of said radiation source while said radiation irradiation circuit allows said radiation source to repeatedly irradiate the radiation and a movable range of said radiation source, wherein said group consisting of parameters further includes an acceleration distance that is the distance, while said radiation source moves during being accelerated, from an imaging preparation position of said radiation source to the imaging start position, and a deceleration distance that is the distance while said radiation source moves during being decelerated, from an irradiation ending position of said radiation source to an imaging ending position.

9. The radiation tomography imaging device according to claim 8, comprising:

an input element inputs said group consisting of said parameters;

wherein said possible imaging range calculation circuit calculates the possible imaging range of said radiation detector based on said group consisting of parameters input in said input element every time when said group consisting of parameters is input into said input element.

10. The radiation tomography imaging device according to claim 8, comprising:

a detector position calculation circuit that calculates a position of said radiation detector.

11. The radiation tomography imaging device according to claim 10, comprising:

an alarm circuit that alarms when a position of said radiation detector calculated by said detector position calculation circuit is out of the possible imaging range of said radiation detector.

12. The radiation tomography imaging device according to claim 10, comprising:
a detector moving control circuit that controls a detector moving system so as to move said radiation detection circuit within the possible imaging range when the position of said radiation detection circuit calculated by said detector position calculation circuit is out of the possible imaging range of said radiation detector.

13. A radiation tomography imaging device, comprising:
a radiation source that irradiates a radiation;
a radiation detector that detects the radiation transmitted through the subject;
a radiation source moving system that moves said radiation source in a body axis direction of a subject;
a radiation irradiation control circuit that controls said radiation source so as to repeatedly irradiate the radiation while said radiation source moving system is moving said radiation source;
an image generation circuit that generates a radiation image using a detection signal output from said radiation detector every radiation irradiation from said radiation source;
a tomography image acquisition circuit that acquires a radiation tomography image by reconstructing a plurality of radiation images generated by said image generation circuit;
a detector moving system that moves in the opposite direction of the moving direction of said radiation source moved by said radiation source moving system while said radiation detector and said radiation source facing each other and sandwiching said subject; and
a possible imaging range calculation circuit that calculates a possible imaging range of said radiation detector, which is a positional range of said radiation detector, wherein said radiation source is in the movable range of said radiation source and said radiation detector can acquire said radiation tomography image based on a group consisting of parameters comprising an imaging distance from the focus point of said radiation source to a detection face of said radiation detector, an irradiation swing angle that is the swing angle of said radiation source while said radiation irradiation circuit allows said radiation source to repeatedly irradiate the radiation, a movable range of said radiation source, and a tomographic section height is a distance from the detection face of said radiation detector to the center of the tomography center point;
wherein said group consisting of parameters further includes an acceleration distance that is the distance, while said radiation source moves during being accelerated, from an imaging preparation position of said radiation source to the imaging start position, and a deceleration distance that is the distance while said radiation source moves during being decelerated, from an irradiation ending position of said radiation source to an imaging ending position.

14. The radiation tomography imaging device according to claim 13, comprising:
an input element inputs said group consisting of said parameters;
wherein said possible imaging range calculation circuit calculates the possible imaging range of said radiation detector based on said group consisting of parameters input in said input element every time when said group consisting of parameters is input into said input element.

15. The radiation tomography imaging device according to claim 13, comprising:
a detector position calculation circuit that calculates a position of said radiation detector.

16. The radiation tomography imaging device according to claim 15, comprising:
an alarm circuit that alarms when a position of said radiation detector calculated by said detector position calculation circuit is out of the possible imaging range of said radiation detector.

17. The radiation tomography imaging device according to claim 15, comprising:
a detector moving control circuit that controls a detector moving system so as to move said radiation detection circuit within the possible imaging range when the position of said radiation detection circuit calculated by said detector position calculation circuit is out of the possible imaging range of said radiation detector.

* * * * *